(12) United States Patent
Takenaka et al.

(10) Patent No.: US 6,346,527 B1
(45) Date of Patent: Feb. 12, 2002

(54) GUANIDINE DERIVATIVES

(75) Inventors: Kohei Takenaka, Sakai; Yoshikazu Inoue, Osaka; Masatoshi Minagawa, Osaka; Atsushi Akahane, Hyogo, all of (JP)

(73) Assignee: Fujisawa Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/674,006
(22) PCT Filed: Apr. 19, 1999
(86) PCT No.: PCT/JP99/02088
§ 371 Date: Oct. 24, 2000
§ 102(e) Date: Oct. 24, 2000
(87) PCT Pub. No.: WO99/55690
PCT Pub. Date: Nov. 4, 1999

(30) Foreign Application Priority Data

Apr. 24, 1998 (AU) .............................................. PP3171
Jan. 25, 1999 (AU) .............................................. PP8311

(51) Int. Cl.[7] .................... C07D 313/08; C07D 279/22; C07D 337/08; C07D 233/16; A61K 31/335
(52) U.S. Cl. .................. 514/213.01; 514/431; 514/450; 514/510; 540/594; 540/595; 549/9; 549/355; 564/237
(58) Field of Search ............................ 514/213.01, 431, 514/450, 510; 540/594, 595; 549/9, 355; 564/237

(56) References Cited

FOREIGN PATENT DOCUMENTS

| EP | 0 640 587 | 3/1995 |
| WO | WO 98/55475 | 12/1998 |
| WO | WO-98/55475 | * 12/1998 |

OTHER PUBLICATIONS

Ng Nephrol. Dial. Transplant 13 (1998) 2994–2996.*
Horikawa et al Jpn. J. Pharmacol. 85 (2001) 272–277 (Medline abstract only).*
Karmazyn Expert Opin. Investig. Drugs 10 (2001) 835–843 (Medline abstract only).*
Karmazyn et al Circ. Res. 85 (1999) 777–786.*
Koren et al Eur. Heart J. 18 (1997) 1296–1299 (Medline abstract only).*

* cited by examiner

*Primary Examiner*—Bruck Kifle
*Assistant Examiner*—Hong Liu
(74) *Attorney, Agent, or Firm*—Oblon, Spivak, McClelland, Maier & Neustadt, P.C.

(57) ABSTRACT

A compound of the formula:

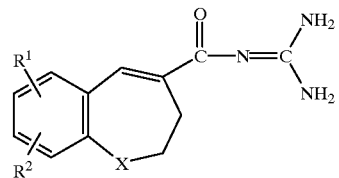

wherein $R^1$ is hydrogen or halogen, $R^2$ is hydroxy, acyl(lower)alkoxy, hydroxy(lower)alkyl, lower alkoxy(lower)alkyl, lower alkylthio(lower)alkyl, mono(or di or tri)halo(lower)alkyl, (ethoxycarbonyl)amino, sulfamoylamino, (dimethylsulfamoyl)amino, N,N-di(lower)alkylamino(lower)alkyl, hydroxyimino(lower)alkyl, lower alkoxyimino(lower)alkyl, acyl, lower alkoxycarbonyl, carbamoyl, di(lower)alkylcarbamoyl, (amino(lower)alkyl)carbamoyl, N,N-di(lower)alkylamino(lower)alkylcarbamoyl, guanidinocarbonyl, morpholinylsulfonyl, sulfamoyl, lower alkylsulfamoyl, (lower alkylsulfonyl)(lower)alkyl, guanidinocarbonyl(lower)alkenyl, lower alkylthio, cyano, acyl(lower)alkyl, acyl(lower)alkenyl, aryl which has one or more substituent(s) or a heterocyclic group which has one or more substituent(s), and X is —O—, or a salt thereof.

7 Claims, No Drawings

GUANIDINE DERIVATIVES

TECHNICAL FIELD

This invention relates to new guanidine derivatives.

One object of this invention is to provide the new and useful guanidine derivatives and salts thereof which possess a strong inhibitory activity on $Na^+/H^+$ exchange in cells.

Another object of this invention is to provide processes for preparation of the guanidine derivatives and salts thereof.

A further object of this invention is to provide a pharmaceutical composition comprising said guanidine derivatives or a pharmaceutically acceptable salt thereof.

Still further object of this invention is to provide a use of said guanidine derivatives or a pharmaceutically acceptable salt thereof as a medicament for the treatment and/or prevention of cardiovascular diseases, cerebrovascular diseases, renal diseases, arteriosclerosis, shock and the like in human being and animals.

BACKGROUND ART

Some guanidine derivatives having pharmaceutical activities such as inhibitory activity on $Na^+/H^+$ exchange in cells have been known as described in WO 98/55475.

DISCLOSURE OF INVENTION

The object guanidine derivatives of the present invention are novel and can be represented by the following general formula (I):

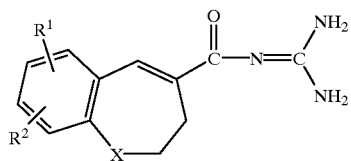
(I)

wherein $R^1$ is hydrogen or halogen, $R^2$ is hydroxy, acyl(lower)alkoxy, hydroxy(lower)alkyl, lower alkoxy(lower)alkyl, lower alkylthio(lower)alkyl, mono(or di or tri)halo(lower)alkyl, (ethoxycarbonyl) amino, sulfamoylamino, (dimethylsulfamoyl)amino, N,N-di(lower)alkylamino(lower)alkyl, hydroxyimino (lower)alkyl, lower alkoxyimino(lower)alkyl, acyl, lower alkylthio, cyano, acyl(lower)alkyl, acyl(lower) alkenyl, aryl which has one or more substituent(s) or a heterocyclic group which has one or more substituent (s), and X is $-CH_2-$, $-S-$, $-SO_2-$, $-O-$ or $-NH-$.

The object compound (I) of the present invention can be prepared by the following process.

Process (1)

(III)
or its reactive derivative at the imino group, or a salt thereof

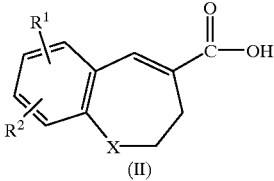
(II)
or its reactive derivative at the carboxy group, or a salt thereof

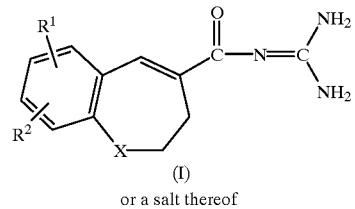
(I)
or a salt thereof wherein $R^1$, $R^2$ and X are each as defined above.

The starting compound (II) can be prepared by the following processes or Preparations mentioned below, or similar manners thereto.

Process (A)

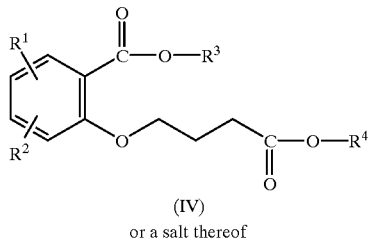
(IV)
or a salt thereof

① cyclization

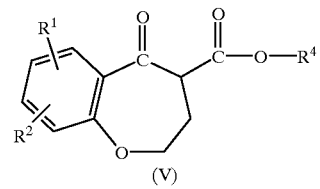
(V)
or a salt thereof

② reduction

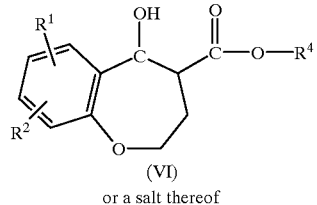
(VI)
or a salt thereof

③ dehydration

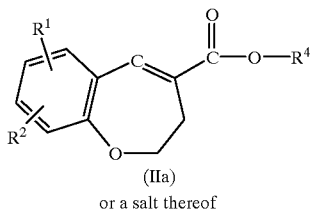

(IIa)

or a salt thereof wherein $R^1$ and $R^2$ are each as defined above, $R^3$ is lower alkyl, and $R^4$ is lower alkyl.

Salts of the object guanidine derivatives (I) are pharmaceutically acceptable, conventional non-toxic salts and may include a salt with a base or an acid addition salt such as a salt with an inorganic base, for example, an alkali metal salt (e.g., sodium salt, potassium salt, etc.), an alkaline earth metal salt (e.g., calcium salt, magnesium salt, etc.), an ammonium salt; a salt with an organic base, for example, an organic amine salt (e.g., triethylamine salt, pyridine salt, picoline salt, ethanolamine salt, triethanolamine salt, triethanolamine salt, dicyclohexylamine salt, N,N'-dibenzylethylenediamine salt, etc.); an inorganic acid addition salt (e.g., hydrochloride, hydrobromide, sulfate, phosphate, etc.); an organic carboxylic or sulfonic acid addition salt (e.g., formate, acetate, trifluoroacetate, maleate, tartrate, citrate, fumarate, isethionate, methanesulfonate, benzenesulfonate, toluenesulfonate, etc.); a salt with a basic or acidic amino acid (e.g., arginine, aspartic acid, glutamic acid, etc.).

In the above and subsequent descriptions of the present specification, suitable examples and illustration of the various definitions which the present invention intends to include within the scope thereof are explained in detail as follows.

The term "lower" is used to intend a group having 1 to 6, preferably 1 to 4, carbon atom(s), unless otherwise provided.

Suitable "lower alkyl" and "lower alkyl" moiety in the terms "hydroxy(lower)alkyl", "hydroxyimino(lower)alkyl", "lower alkylthio", etc. may include straight or branched one having 1 to 6 carbon atom(s), such as methyl, ethyl, propyl, isopropyl, butyl, isobutyl, sec-butyl, tert-butyl, pentyl, tert-pentyl, hexyl, and the like, preferably one having 1 to 4 carbon atom(s).

Suitable "lower alkenyl" and "lower alkenyl" moiety in the term "acyl(lower)alkenyl" may include vinyl, 1-(or 2-)propenyl, 1-(or 2- or 3-)butenyl, 1-(or 2- or 3- or 4-)pentenyl, 1-(or 2- or 3- or 4- or 5-)hexenyl, methylvinyl, ethylvinyl, 1-(or 2- or 3-)methyl-1-(or 2-)propenyl, 1-(or 2- or 3-)ethyl-1-(or 2-)propenyl, 1-(or 2- or 3- or 4-)methyl-1-(or 2- or 3-)butenyl, and the like, in which more preferable example may be $C_2$–$C_4$ alkenyl.

Suitable "lower alkoxy" and "lower alkoxy" moiety in the terms "acyl(lower)alkoxy", "lower alkoxy(lower)alkyl" and "lower alkoxyimino(lower)alkyl" may include methoxy, ethoxy, propoxy, isopropoxy, butoxy, isobutoxy, t-butoxy, pentyloxy, t-pentyloxy, hexyloxy and the like, in which the preferred one may be $C_1$–$C_4$ alkoxy.

Suitable "halogen" may include fluorine, bromine, chlorine and iodine.

Mono(or di or tri)halo(lower)alkyl may include fluoromethyl, difluoromethyl, trifluoromethyl, chloromethyl, dichloromethyl, trichloromethyl, bromomethyl, dibromomethyl, tribromomethyl, 1 or 2-fluoroethyl, 1 or 2-bromoethyl, 1 or 2-chloroethyl, 1,1-difluoroethyl, 2,2-difluoroethyl and the like, in which the preferred one is trifluoromethyl.

Suitable "aryl" may include phenyl, naphthyl and the like.

Suitable "acyl" and "acyl" moiety in the terms "acyl(lower)alkoxy", "acylamino" and "acyl(lower)alkenyl" may include carboxy, carbamoyl, aliphatic acyl group and acyl group containing an aromatic ring, which is referred to as aromatic acyl, or heterocyclic ring, which is referred to as heterocyclic acyl.

Suitable example of said acyl may be illustrated as follows:

Carboxy; Carbamoyl; Thiocarbamoyl; Sulfamoyl;

Aliphatic acyl such as lower or higher alkanoyl (e.g., formyl, acetyl, propanoyl, butanoyl, 2-methylpropanoyl, pentanoyl, 2,2-dimethylpropanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl, icosanoyl, etc.);

lower or higher alkoxycarbonyl (e.g., methoxycarbonyl, ethoxycarbonyl, t-butoxycarbonyl, t-pentyloxycarbonyl, heptyloxycarbonyl, etc.);

lower or higher alkylsulfonyl (e.g., methylsulfonyl, ethylsulfonyl, etc.);

lower or higher alkylsulfinyl (e.g., methylsulfinyl, ethylsulfinyl, etc.);

lower or higher alkoxysulfonyl (e.g., methoxysulfonyl, ethoxysulfonyl, etc.);

lower or higher alkoxysulfinyl (e.g., methoxysulfinyl, ethoxysulfinyl, etc.);

mono(or di or tri)halo(lower)alkylsulfonyl [e.g. fluoromethylsulfonyl, difluoromethylsulfonyl, trifluoromethylsulfonyl, chloromethylsulfonyl, dichloromethylsulfonyl, trichloromethylsulfonyl, 1 or 2-fluoroethylsulfonyl, 1 or 2-chloroethylsulfonyl, etc.);

mono(or di or tri)halo(lower)alkylsulfinyl [e.g. fluoromethylsulfinyl, difluoromethylsulfinyl, trifluoromethylsulfinyl, chloromethylsulfinyl, dichloromethylsulfinyl, trichloromethylsulfinyl, 1 or 2-fluoroethylsulfinyl, 1 or 2-chloroethylsulfinyl, etc.); or the like;

Aromatic acyl such as aroyl (e.g., benzoyl, toluoyl, naphthoyl, etc.);

ar(lower)alkanoyl [e.g., phenyl(lower)alkanoyl (e.g., phenylacetyl, phenylpropanoyl, phenylbutanoyl, phenylisobutanoyl, phenylpentanoyl, phenylhexanoyl, etc.), naphthyl(lower)alkanoyl (e.g., naphthylacetyl, naphthylpropanoyl, naphthylbutanoyl, etc.), etc.];

ar(lower)alkenoyl [e.g., phenyl(lower)alkenoyl (e.g., phenylpropenoyl, phenylbutenoyl, phenylmethacryloyl, phenylpentenoyl, phenylhexenoyl, etc.), naphthyl(lower)alkenoyl (e.g., naphthylpropenoyl, naphthylbutenoyl, etc.), etc.];

ar(lower)alkoxycarbonyl [e.g., phenyl(lower)alkoxycarbonyl (e.g., benzyloxycarbonyl, etc.), etc.];

aryloxycarbonyl (e.g., phenoxycarbonyl, naphthyloxycarbonyl, etc.);

aryloxy(lower)alkanoyl (e.g., phenoxyacetyl, phenoxypropionyl, etc.);

arylglyoxyloyl (e.g., phenylglyoxyloyl, naphthylglyoxyloyl, etc.);

arylsulfonyl (e.g., phenylsulfonyl, p-tolylsulfonyl, etc.);

arylsulfinyl (e.g., phenylsulfinyl, p-tolylsulfinyl, etc.); or the like;

Heterocyclic acyl such as heterocycliccarbonyl;

heterocyclicsulfonyl;

heterocyclic(lower)alkanoyl (e.g., heterocyclicacetyl, heterocyclicpropanoyl, heterocyclicbutanoyl, heterocyclicpentanoyl, heterocyclichexanoyl, etc.);

heterocyclic(lower)alkenoyl (e.g., heterocyclicpropenoyl, heterocyclicbutenoyl, heterocyclicpentenoyl, heterocyclichexenoyl, etc.); heterocyclicglyoxyloyl; or the like.

Suitable "heterocyclic" and "heterocyclic" moiety in the terms "heterocycliccarbonyl", "heterocyclic(lower) alkanoyl", heterocyclic(lower)alkenoyl", "heterocyclicglyoxyloyl", etc. may include saturated or unsaturated, monocyclic or polycyclic heterocyclic group containing at least one hetero-atom such as an oxygen, sulfur, nitrogen atom and the like.

And, especially preferable heterocyclic group may be heterocyclic group such as unsaturated 3 to 8-membered (more preferably 5 or 6-membered) heteromonocyclic group containing 1 to 4 nitrogen atom(s), for example, pyrrolyl, pyrrolinyl, imidazolyl, pyrazolyl, pyridyl, dihydropyridyl, pyrimidinyl, pyrazinyl, pyridazinyl, triazolyl (e.g., 4H-1,2,4-triazolyl, 1H-1,2,3-triazolyl, 2H-1,2,3-triazolyl, etc.), tetrazolyl (e.g., 1H-tetrazolyl, 2H-tetrazolyl, etc.), etc.;

saturated 3 to 8-membered (more preferably 5 or 6-membered) heteromonocyclic group containing 1 to 4 nitrogen atom(s), for example, pyrrolidinyl, imidazolidinyl, piperidyl, piperazinyl, etc.;

unsaturated condensed heterocyclic group containing 1 to 4 nitrogen atom(s), for example, indolyl, isoindolyl, indolinyl, indolizinyl, benzimidazolyl, quinolyl, isoquinolyl, indazolyl, benzotriazolyl, etc.;

unsaturated 3 to 8-membered (more preferably 5 or 6-membered) heteromonocyclic group containing 1 to 2 oxygen atom(s) and 1 to 3 nitrogen atom(s), for example, oxazolyl, isoxazolyl, oxadiazolyl (e.g., 1,2,4-oxadiazolyl, 1,3,4-oxadiazolyl, 1,2,5-oxadiazolyl, etc.), etc.;

saturated 3 to 8-membered (more preferably 5 or 6-membered) heteromonocyclic group containing 1 to 2 oxygen atom(s) and 1 to 3 nitrogen atom(s), for example, oxazolidinyl, morpholinyl, sydnonyl, etc.;

unsaturated condensed heterocyclic group containing 1 to 2 oxygen atom(s) and 1 to 3 nitrogen atom(s), for example, benzoxazolyl, benzoxadiazolyl, etc.;

unsaturated 3 to 8-membered (more preferably 5 or 6-membered) heteromonocyclic group containing 1 to 2 sulfur atom(s) and 1 to 3 nitrogen atom(s), for example, thiazolyl, isothiazolyl, thiadiazolyl (e.g., 1,2,3-thiadiazolyl, 1,2,4-thiadiazolyl, 1,3,4-thiadiazolyl, 1,2,5-thiadiazolyl, etc.), dihydrothiazinyl, etc.;

saturated 3 to 8-membered (more preferably 5 or 6-membered) heteromonocyclic group containing 1 to 2 sulfur atom(s) and 1 to 3 nitrogen atom(s), for example, thiazolidinyl, etc.;

unsaturated 3 to 8-membered (more preferably 5 or 6-membered) heteromonocyclic group containing 1 to 2 sulfur atom(s), for example, thienyl, dihydrodithiinyl, dihydrodithionyl, etc.;

unsaturated condensed heterocyclic group containing 1 to 2 sulfur atom(s) and 1 to 3 nitrogen atom(s), for example, benzothiazolyl, benzothiadiazolyl, etc.;

unsaturated 3 to 8-membered (more preferably 5 or 6-membered) heteromonocyclic group containing an oxygen atom, for example, furyl, etc.;

unsaturated 3 to 8-membered (more preferably 5 or 6-membered) heteromonocyclic group containing an oxygen atom and 1 to 2 sulfur atom(s), for example, dihydrooxathiinyl, etc.;

unsaturated condensed heterocyclic group containing 1 to 2 sulfur atom(s), for example, benzothienyl, benzodithiinyl, etc.;

unsaturated condensed heterocyclic group containing an oxygen atom and 1 to 2 sulfur atom(s), for example, benzoxathiinyl, etc.; and the like.

The acyl moiety as stated above may have 1 to 10 (preferably 1 to 4), same or different, suitable substituent(s) such as lower alkyl as exemplified above; lower alkoxy as exemplified above; lower alkylthio wherein lower alkyl moiety is as exemplified above; lower alkylamino wherein lower alkyl moiety is as exemplified above; halogen; amino; protected amino (e.g., acylamino, benzylamino, tritylamino, etc.); guanidino; hydroxy; cyano; nitro; carboxy; sulfo; sulfamoyl; imino; oxo; amino(lower)alkyl wherein lower alkyl moiety is as exemplified above; carbamoyloxy; hydroxy(lower)alkyl wherein lower alkyl moiety is as exemplified above; diamino(lower)alkylidene (e.g., diaminomethylene, etc.); di(lower)alkylamino wherein lower alkyl moiety is as exemplified above; di(lower)alkylamino(lower)alkyl wherein lower alkyl moiety is as exemplified above, or the like.

Suitable "substituent" in the terms "aryl which may have one or more substituent(s)", wherein the preferable number of substituent(s) is 1 to 4, and the more preferable one is 1 or 2, and "a heterocyclic group which may have one or more substituent(s)", wherein the preferable number of substituent (s) is 1 to 4, and the more preferable one is 1 or 2, may include lower alkyl, lower alkoxy, lower alkenyl, lower alkynyl (e.g., ethynyl, 1-propynyl, propargyl, 1-methylpropargyl, 1-methylpropargyl, 1 or 2 or 3-butynyl, 1 or 2 or 3 or 4-pentynyl, 1 or 2 or 3 or 4 or 5-hexynyl, etc.), mono(or di or tri)halo(lower)alkyl (e.g., fluoromethyl, difluoromethyl, trifluoromethyl, chloromethyl, dichloromethyl, trichloromethyl, bromomethyl, dibromomethyl, tribromomethyl, 1 or 2-fluoroethyl, 1 or 2-bromoethyl, 1 or 2-chloroethyl, 1,1-difluoroethyl, 2,2-difluoroethyl, etc.), halogen, carboxy, hydroxy, aryl, ar(lower)alkyl such as phenyl(lower)alkyl (e.g., benzyl, phenethyl, phenylpropyl, etc.), carboxy(lower)alkyl, nitro, amino, di(lower)alkylamino (e.g., dimethylamino, diethylamino, diisopropylamino, ethylmethylamino, isopropylmethylamino, ethylmethylamino, ethylpropylamino, etc.), hydroxy(lower)alkyl, acyl, cyano, mercapto, lower alkylthio (e.g., methylthio, ethylthio, propylthio, isopropylthio, butylthio, etc.), imino, oxo, and the like.

The process for preparing the object compound and the starting compound of the present invention is explained in detail in the following.

Process (1)

The compound (I) or a salt thereof can be prepared by reacting the compound (II) or its reactive derivative at the carboxy group, or a salt thereof with the compound (III) or its reactive derivative at the imino group, or a salt thereof.

Suitable reactive derivative at the imino group of the compound (III) may include a silyl derivative formed by the reaction of the compound (III) with a silyl compound such as bis(trimethylsilyl)acetamide, mono(trimethylsilyl) acetamide [e.g. N-(trimethylsilyl)acetamide], bis (trimethylsilyl)urea or the like; a derivative formed by reaction of the compound (III) with phosphorus trichloride or phosgene, and the like.

Suitable salts of the compound (II) and its reactive derivative can be referred to the ones as exemplified for the compound (I).

Suitable reactive derivative at the carboxy group of the compound (II) may include a conventional one such as an acid halide, an acid anhydride, an activated amide, an activated ester, and the like.

Suitable examples of the reactive derivatives may be an acid chloride; an acid azide; a mixed acid anhydride with an acid such as substituted phosphoric acid [e.g. dialkylphosphoric acid, phenylphosphoric acid, diphenylphosphoric acid, dibenzylphosphoric acid halogenated phosphoric acid, etc.], dialkylphosphorous acid, sulfurous acid, thiosulfuric acid, sulfuric acid, sulfonic acid [e.g. methanesulfonic acid, etc.], aliphatic carboxylic acid [e.g. acetic acid, propionic acid, butyric acid, isobutyric acid, pivalic acid, pentanoic acid, isopentanoic acid, 2-ethylbutyric acid, trichloroacetic acid, etc.] or aromatic carboxylic acid [e.g. benzoic acid, etc.]; a symmetrical acid anhydride; an activated amide with imidazole, 1-hydroxy-1H-benzotriazole, 4-substituted imidazole, dimethylpyrazole, triazole or tetrazole; or an activated ester [e.g. cyanomethyl ester, methyl ester, ethyl ester, methoxymethyl ester, dimethyliminomethyl

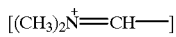

ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, benzothiazolyl thioester, carboxymethyl thioester, pyranyl ester, pyridyl ester, piperidyl ester, 8-quinolyl thioester, etc.], or an ester with a N-hydroxy compound [e.g. N,N-dimethylhydroxylamine, 1-hydroxy-2-(1H)-pyridone, N-hydroxysuccinimide, N-hydroxyphthalimide, 1-hydroxy-1H-benzotriazole, etc.], and the like. These reactive derivatives can optionally be selected from them according to the kind of the compound (II) to be used.

Suitable salts of the compound (III) and its reactive derivative can be referred to the ones as exemplified for the compound (I).

The reaction is usually carried out in a conventional solvent such as water, alcohol [e.g. methanol, ethanol, etc.], acetone, dioxane, acetonitrile, chloroform, methylene chloride, ethylene chloride, tetrahydrofuran, ethyl acetate, N,N-dimethylformamide, pyridine or any other organic solvent which does not adversely influence the reaction. These conventional solvent may also be used in a mixture with water.

In this reaction, when the compound (II) is used in a free acid form or its salt form, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carboxiimide; N,N'-diethylcarbodiimide, N,N'-diisopropylcarbodiimide; N-ethyl-N'-(3-dimethylaminopropyl)carbodiimide; N,N'-carbonyl-bis(2-methylimidazole); pentamethyleneketene-N-cyclohexylimine; diphenylketene-N-cyclohexylimine; ethoxyacetylene; 1-alkoxy-1-chloroethylene; trialkyl phosphite; ethyl polyphosphate; isopropyl polyphosphate; phosphorus oxychloride (phosphoryl chloride); phosphorus trichloride; thionyl chloride; oxalyl chloride; lower alkyl haloformate [e.g. ethyl chloroformate, isopropyl chloroformate, etc.]; triphenylphosphine; 2-ethyl-7-hydroxybenzisoxazolium salt; 2-ethyl-5-(m-sulfophenyl) isoxazolium hydroxide intramolecular salt; 1-(p-chlorobenzenesulfonyloxy)-6-chloro-1H-benzotriazole; a combination of N-lower alkylhalopyridium halide (e.g., 1-methyl-2-chloropyridinium iodide, etc.) and tri(lower) alkylamine (e.g. triethylamine, etc.); so-called Vilsmeier reagent prepared by the reaction of N,N-dimethylformamide with thionyl chloride, phosgene, trichloromethyl chloroformate, phosphorus oxychloride, etc.; or the like.

The reaction may also be carried out in the presence of an inorganic or organic base such as an alkali metal bicarbonate, tri(lower)alkylamine (e.g. triethylamine, etc.), pyridine, N-(lower)alkylmorpholine, N,N-di(lower) alkylbenzylamine, alkali metal lower alkoxide (e.g. sodium methoxide, etc.) or the like.

The reaction temperature is not critical, and the reaction is usually carried out under cooling to warming.

Process (A)-④

The compound (V) or a salt thereof can be prepared by subjecting the compound (IV) or a salt thereof to cyclization reaction.

This reaction can be carried out in the manner disclosed in Preparation 20 or similar manners thereto.

Process (A)-②

The compound (VI) or a salt thereof can be prepared by subjecting the compound (V) or a salt thereof to reduction reaction.

This reaction can be carried out in the manner disclosed in Preparation 22 or similar manners thereto.

Process (A)-③

The compound (IIa) or a salt thereof can be prepared by subjecting the compound (VI) or a salt thereof to dehydration reaction.

This reaction can be carried out in the manner disclosed in Preparation 24 or similar manner thereto.

It is to be noted that the object compound (I) may include one or more stereoisomer(s) due to asymmetric carbon atom(s) and double bond(s) and all such isomers and mixture thereof are included within the scope of this invention.

Regarding the object compound (I), it is to be understood that they include tautomeric isomers.

That is, a group of the formula:

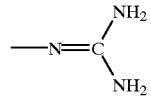

can be also alternatively represented by its tautomeric formula:

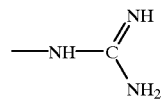

That is, both of the said groups are in the state of equilibrium and such tautomerism can be represented by the following equilibrium.

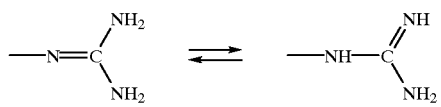

And it is obvious to any person skilled in the arts that both of the tautomeric isomers are easily convertible reciprocally and are included within the same category of the compound per se.

Accordingly, the both of the tautomeric forms of the object compound (I) are clearly included within the scope of the present invention.

In the present specification, the object compound including the group of such tautomeric isomers is represented by using one of the expressions therefor, that is the formula:

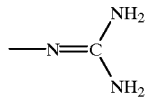

only for the convenient sake.

It is further to be noted that isomerization or rearrangement of the object compound (I) may occur due to the effect of the light, acid, base or the like, and the compound obtained as the result of said isomerization or rearrangement is also included within the scope of the present invention.

It is also to be noted that the solvating form of the compound (I) (e.g. hydrate, etc.) and any form of the crystal of the compound (I) are included within the scope of the present invention.

The new guanidine derivatives (I) and a pharmaceutically acceptable salt thereof of the present invention possess a strong inhibitory activity on $Na^+/H^+$ exchange in cells and therefore are useful as an inhibitor on $Na^+/H^+$ exchange in cells.

Accordingly, the new guanidine derivatives (I) and a pharmaceutically acceptable salt thereof can be used for the expectorant and for the treatment and/or prevention of cardiovascular diseases [e.g. hypertension, angina pectoris, myocardial infarction, heart failure (e.g. congestive heart failure, acute heart failure, cardiac hypertrophy, etc.), arrhythmia (e.g. ischemic arrhythmia, arrhythmia due to myocardial infarction, arrhythmia after PTCA (percutaneous transluminal coronary angioplasty), thrombolysis or CABG (coronary artery bypass graft), etc.), restenosis after PTCA or PTA (percutaneous transluminal angioplasty), etc.], cerebrovascular diseases [e.g. ischemic stroke, hemorrhagic stroke, edema, etc.], renal diseases [e.g. diabetic nephropathy, ischemic acute renal failure, etc.], arteriosclerosis, shock [e.g. hemorrhagic shock, endotoxin shock, etc.], hyperlipidemia and the like, and can also be used as an agent for ischemic reperfusion injury, myocardial protection, organ protection in organ transplantation, in non-cardiac and cardiac surgery, and the like.

In order to show the utilities of the guanidine derivatives (I) and a pharmaceutically acceptable salt thereof of the present invention, pharmacological test data of the representative compound of the guanidine derivatives (I) are illustrated in the following.

[1] Test Compound
(a) [9-[(E)-(2-Carboxyvinyl)]-2,3-dihydro-1-benzoxepin-4-carbonyl]guanidine hydrochloride

[2] Inhibitory activity on $Na^+/H^+$ exchange in cells
[i] Test Method

Procedure was carried out according to a similar manner to the method described in Enzymology 173, 777 (1989).
Cell preparation: One male SD strain rat weighing 250–300 g was sacrificed with the blow on the head. Then, the thymus was removed into ice-cold NaCl medium (140 mM sodium chloride, 1 mM potassium chloride, 1 mM calcium chloride, 1 mM magnesium chloride, 10 mM glucose and 20 mM N-2-hydroxyethylpiperazine-N'-2-ethanesulfonic acid (HEPES)—pH 7.3), cut in small fragments, and transferred to glass homogenizer. The cells were dissociated by gentle strokes, and the resulting suspension was filtrated through six layers of surgical gauze and the filtrate was centrifuged at 4° C. at 1000 g for 10 minutes.

Assay: The pellet was washed with Na-free buffer (140 mM Trimethyl ammonium, 4 mM KCl, 1 mM $CaCl_2$, 1 mM $MgSO_4$, 1 mM $NaH_2PO_4$, 18 mM glucose, 20 mM HEPES (pH 7.4)), then incubated with 16 μM of acetoxymethyl ester of 2', 7'-bis(2-carboxyethyl)-5,6-carboxyfluorescein (BCECF-AM, Calbiochem Co.) and 20 mM $NH_4Cl$ at 37° C. for 30 minutes. The BCECF- and $NH_4Cl$-loaded cells were washed twice, resuspended in Na-free buffer and kept at 4° C. Intracellular pH was measured at 37° C. with a spectrofluorometer (FS100, Kowa company, Japan) using the ratio of the emission (530 nm) obtained at 490 nm excitation wavelengths. After addition of 10 μl cell suspension into 460 μl of Na-free buffer including test compound solved in dimethyl sulfoxide (final concentration of dimethyl sulfoxide was 0.1%), 25 μl of 2.0 M NaCl (final 100 mM) was applied to start the reaction. The initial increase in intracellular pH in response to the added NaCl was taken as an estimate of $Na^+/H^+$ exchange activity. The BCECF fluorescence signals were calibrated by titration with 1 M 2-(N-morpholino)ethanesulfonic acid (MES) after permeabilization of the cells with 0.5% Triton.

[3] Test Result:

| Test Compound | $IC_{50}$ (M) |
|---|---|
| (a) | $<1.0 \times 10^{-7}$ |

The object compound (I) or its pharmaceutically acceptable salts can usually be administered to mammals including human being in the form of a conventional pharmaceutical composition such as oral dosage form (e.g., capsule, microcapsule, tablet, granule, powder, troche, syrup, aerosol, inhalation, suspension, emulsion, etc.), injection dosage form, suppository, ointment, or the like.

The pharmaceutical composition of this invention can contain various organic or inorganic carrier materials, which are conventionally used for pharmaceutical purpose such as excipient (e.g., sucrose, starch, mannit, sorbit, lactose, glucose, cellulose, talc, calcium phosphate, calcium carbonate, etc.), binding agent (e.g., cellulose, methyl cellulose, hydroxypropylcellulose, polypropylpyrrolidone, gelatin, gum arabic, polyethyleneglycol, sucrose, starch, etc.), disintegrator (e.g., starch, carboxymethyl cellulose, calcium salt of carboxymethyl cellulose, hydroxypropylstarch, sodium glycolestarch, sodium bicarbonate, calcium phosphate, calcium citrate, etc.), lubricant (e.g., magnesium stearate, talc, sodium laurylsulfate, etc.), flavoring agent (e.g., citric acid, menthol, glycine, orange powders, etc.), preservative (e.g., sodium benzoate, sodium bisulfite, methylparaben, propylparaben, etc.), stabilizer (e.g., citric acid, sodium citrate, acetic acid, etc.), suspending agent (e.g., methyl cellulose, polyvinylpyrrolidone, aluminum stearate, etc.), dispersing agent, aqueous diluting agent (e.g., water, etc.), base wax (e.g., cacao butter, polyethyleneglycol, white petrolatum, etc.).

The effective ingredient may usually be administered with a unit dose of 0.01 mg/kg to 500 mg/kg, 1 to 4 times a day. However, the above dosage may be increased or decreased according to age, weight, conditions of the patient or the administering method.

Preferred embodiments of the object compound (I) are as follows.

R¹ is hydrogen or halogen (more preferably chroline),
R² is hydroxy, lower alkoxycarbonyl(lower)alkoxy (more preferably $C_1$–$C_4$ alkoxycarbonyl-($C_1$–$C_4$)alkoxy, most preferably methoxycarbonylmethoxy), hydroxy(lower)alkyl (more preferably hydroxy($C_1$–$C_4$)alkoxy, most preferably hydroxymethyl), lower alkoxy(lower)alkyl (more preferably $C_1$–$C_4$ alkoxy($C_1$–$C_4$)alkyl, most preferably methoxymethyl), lower alkylthio(lower)alkyl (more preferably $C_1$–$C_4$ alkylthio($C_1$–$C_4$)alkyl, most preferably methylthiomethyl), dihalo(lower)alkyl (more preferably dihalo-($C_1$–$C_4$)alkyl, most preferably difluoromethyl), trihalo(lower)alkyl (more preferably trihalo($C_1$–$C_4$)alkyl, most preferably trifluoromethyl), (ethoxycarbonyl)amino, sulfamoylamino, (dimethylsulfamoyl)amino, N,N-di(lower)alkylamino (lower)alkyl (more preferably N,N-di($C_1$–$C_4$) alkylamino)$C_1$–$C_4$)alkyl, most preferably N,N-dimethylaminomethyl), hydroxyimino(lower)alkyl (more preferably hydroxyimino($C_1$–$C_4$)alkyl, most preferably hydroxyiminomethyl), lower alkoxyimino (lower)alkyl (more preferably $C_1$–$C_4$ alkoxyimino ($C_1$–$C_4$)alkyl, most preferably methoxyiminomethyl), carboxy, lower alkoxycarbonyl (more preferably $C_1$–$C_4$ alkoxycarbonyl, most preferably methoxycarbonyl), carbamoyl, di(lower) alkylcarbamoyl (more preferably di($C_1$–$C_4$) alkylcarbamoyl, most preferably dimethylcarbamoyl), (amino(lower)alkyl)carbamoyl (more preferably (amino($C_1$–$C_4$)alkyl)carbamoyl, most preferably (2-aminoethyl)carbamoyl, N,N-di(lower)alkylamino (lower)alkylcarbamoyl (more preferably N,N-di ($C_1$–$C_4$)alkylamino($C_1$–$C_4$)-alkylcarbamoyl, most preferably (2-(dimethylamino)ethyl)carbamoyl), guanidinocarbonyl, lower alkylsulfonyl (more preferably $C_1$–$C_4$ alkylsulfonyl, most preferably methylsulfonyl), lower alkylsulfinyl (more preferably $C_1$–$C_4$ alkylsulfinyl, most preferably methylsulfinyl), morpholinylsulfonyl (more preferably morpholinosulfonyl), sulfamoyl, lower alkylsulfamoyl (more preferably $C_1$–$C_4$ alkylsulfamoyl, most preferably methylsulfamoyl or ethylsulfamoyl), lower alkylthio (more preferably $C_1$–$C_4$ alkylthio, most preferably methylthio or ethylthio), cyano, (lower alkylsulfonyl) (lower)alkyl (more preferably ($C_1$–$C_4$)alkylsulfonyl) ($C_1$–$C_4$)alkyl, most preferably (methylsulfonyl) methyl), carboxy(lower)alkenyl (more preferably carboxy($C_2$–$C_4$)alkenyl, most preferably carboxyvinyl), guanidinocarbonyl(lower)alkenyl (more preferably guanidinocarbonyl($C_2$–$C_4$)-alkenyl, most preferably guanidinocarbonylvinyl), aryl which has one or two hydroxy(lower)alkyl (more preferably (hydroxy($C_1$–$C_4$)alkyl)phenyl, most preferably (hydroxymethyl)phenyl), or a heterocyclic group (more preferably unsaturated 3 to 8-membered (more preferably 5 or 6-membered) heteromonocyclic group containing 1 to 2 sulfur atom(s) or saturated 3 to 8-membered (more preferably 5 or 6-membered) heteromonocyclic group containing 1 to 4 nitrogen atom (s), most preferably thienyl or pyrrolidinyl) which has one or two halogen or oxo (more preferably dihalothienyl (most preferably dichlorothienyl) or oxopyrrolidinyl), and X is —O—.

More preferred embodiments of the object compound (I) are as follows.

R¹ is hydrogen or halogen,
R² is guanidinocarbonyl or lower alkylsulfonyl, and
X is —O—.

The following Preparations and Examples are given for the purpose of illustrating the present invention in more detail. The solvents indicated between parentheses after the melting point represent the crystallization solvents.

Preparation 1

A mixture of ethyl 2,3-dihydro-9-iodo-1-benzoxepin-4-carboxylate (0.34 g), ethyl acrylate (0.13 ml), palladium(II) acetate (2.2 mg), tri-o-tolylphosphine (6.0 mg), and triethylamine (0.15 ml) in acetonitrile (1 ml) was stirred at 100° C. under nitrogen atmosphere for 5 hours and partitioned between ethyl acetate and water. The organic layer was washed successively with water and brine, dried over anhydrous magnesium sulfate, and evaporated in vacuo. The residue was triturated in n-hexane to give a solid of ethyl 2,3-dihydro-9-[(E)-(2-ethoxycarbonylvinyl)]-1-benzoxepin-4-carboxylate (0.14 g).

mp: 96–97° C.

IR (KBr): 1712, 1689, 1628, 1583 cm$^{-1}$

NMR (DMSO-$d_6$, δ): 1.34 (3H, t, J=7.1 Hz), 1.35 (3H, t, J=7.1 Hz), 2.95–3.1 (2H, m), 4.2–4.45 (4H, m), 6.47 (1H, d, J=16.2 Hz), 7.04 (1H, dd, J=7.7, 7.7 Hz), 7.38 (1H, dd, J=1.6, 7.7 Hz), 7.51 (1H, dd, J=1.6, 7.7 Hz), 7.58 (1H, s), 8.08 (1H, d, J=16.2 Hz)

APCI-MS: 317 [M+H]$^+$

Preparation 2

The following compound was obtained according to a similar manner to that of Preparation 1.

Ethyl 9-[(E)-(2-tert-butoxycarbonylvinyl)]-2,3-dihydro-1-benzoxepin-4-carboxylate NMR (CDCl$_3$, δ): 1.35 (3H, t, J=7.1 Hz), 1.54 (9H, s), 2.9–3.05 (2H, m), 4.28 (2H, q, J=7.1 Hz), 4.3–4.4 (2H, m), 6.39 (1H, d, J=16.1 Hz), 7.02 (1H, dd, J=7.7, 7.7 Hz), 7.36 (1H, dd, J=1.5, 7.7 Hz), 7.50 (1H, dd, J=1.5, 7.7 Hz), 7.57 (1H, s), 7.99 (1H, d, J=16.1 Hz)

Preparation 3

To a solution of ethyl 9-[(E)-(2-tert-butoxycarbonylvinyl)]-2,3-dihydro-1-benzoxepin-4-carboxylate (0.56 g) was added trifluoroacetic acid (0.63 ml) at 0° C. The reaction mixture was stirred overnight at ambient temperature and evaporated in vacuo. The residue was triturated with diisopropyl ether to give a solid of ethyl 9-[(E)-(2-carboxyvinyl)]-2,3-dihydro-1-benzoxepin-4-carboxylate (0.3 g).

mp: 166–168° C.

IR (KBr): 1703, 1682, 1620, 1581 cm$^{-1}$

NMR (DMSO-$d_6$, δ): 1.28 (3H, t, J=7.1 Hz), 2.85–3.0 (2H, m), 4.21 (2H, q, J=7.1 Hz), 4.3–4.45 (2H, m), 6.53 (1H, d, J=16.2 Hz), 7.10 (1H, dd, J=7.7, 7.7 Hz), 7.53 (1H, s), 7.55–7.65 (1H, m), 7.65–7.8 (1H, m), 7.92 (1H, d, J=16.2 Hz)

APCI-MS: 289 [M+H]$^+$

Preparation 4

The following compound was obtained according to a similar manner to that of Preparation 3.

Ethyl 9-carboxymethoxy-2,3-dihydro-1-benzoxepin-4-carboxylate mp: 100–101° C.

IR (KBr): 1740, 1700 cm$^{-1}$

NMR (DMSO-$d_6$, δ): 1.27 (3H, t, J=7.1 Hz), 2.8–2.95 (2H, m), 4.1–4.35 (2H, m), 4.68 (2H, s), 6.85–7.15 (3H, m), 7.50 (1H, s), 12.99 (1H, br s)

APCI-MS: 293 [M+H]$^+$

Preparation 5

A mixture of ethyl 2,3-dihydro-9-iodo-1-benzoxepin-4-carboxylate (1.03 g), 2-formylbenzeneboronic acid (0.49 g), tetrakis(triphenylphosphine)palladium(0) (0.35 g), and triethylamine (0.92 ml) in N,N-dimethylformamide (10.3 ml) was stirred at 100° C. under nitrogen atomsphere for 2.5 hours and partitioned between ethyl acetate and water. The organic layer was washed successively with 1N hydrochloric acid, saturated aqueous sodium bicarbonate, and brine, dried over anhydrous magnesium sulfate, and evaporated in vacuo. The residue was purified by medium pressure liquid chromatography (silica gel) using a mixture of ethyl acetate and n-hexane (1:30~1:9) to give a solid of ethyl 2,3-dihydro-9-(2-formylphenyl)-1-benzoxepin-4-carboxylate (0.63 g).

mp : 83–85° C.

IR (KBr) : 1695, 1633, 1595 $cm^{-1}$

NMR ($CDCl_3$, δ) : 1.35 (3H, t, J=7.1Hz), 2.8–3.0 (2H, m), 4.05–4.25 (2H, m), 4.28 (2H, q, J=7.1Hz), 7.14 (1H, dd, J=7.5, 7.5Hz), 7.2–7.35 (2H, m), 7.35–7.55 (2H, m), 7.6–7.75 (2H, m), 7.95–8.1 (1H, m), 9.84 (1H, s)

Preparation 6

The following compound was obtained according to a similar manner to that of Preparation 5.

Ethyl 9-(2,5-dichloro-3-thienyl)-2,3-dihydro-1-benzoxepin-4-carboxylate

IR (Film) : 1703, 1633 $cm^{-1}$

NMR (DMSO-$d_6$, δ) : 1.35 (3H, t, J=7.1Hz), 2.9–3.05 (2H, m), 4.2–4.4 (4H, m), 6.82 (1H, s), 7.05–7.15 (1H, m), 7.2–7.45 (2H, m), 7.62 (1H, s)

APCI-MS : 369, 371 $[M+H]^+$

Preparation 7

To a solution of ethyl 2,3-dihydro-9-(2-formylphenyl)-1-benzoxepin-4-carboxylate (0.58 g) in a mixture of ethanol (5.8 ml) and tetrahydrofuran (3 ml) was added sodium borohydride (34 mg) at 0 C. The reaction mixture was stirred for 30 minutes at ambient temperature, thereto was added 1N hydrochloric acid (2 ml), and evaporated in vacuo. The residue was partitioned between ethyl acetate and water. The organic layer was washed successively with saturated aqueous sodium bicarbonate and brine, dried over anhydrous magnesium sulfate, and evaporated n vacuo. The residue was purified by medium pressure liquid chromatography (silica gel) using a mixture of ethyl acetate and n-hexane (1:9) as an eluent to give a solid of ethyl 2,3-dihydro-9-(2-hydroxymethylphenyl)-1-benzoxepin-4-carboxylate (530 mg).

mp : 94–95° C.

IR (KBr) : 3357, 1703, 1631 $cm^{-1}$

NMR (DMSO-$d_6$, δ) : 1.35 (3H, t, J=7.1Hz), 1.92 (1H, br s), 2.85–3.0 (2H, m), 3.95–4.2 (2H, m), 4.28 (2H, q, J=7.1Hz), 4.35–4.55 (2H, m), 7.05–7.25 (3H, m), 7.3–7.5 (3H, m), 7.5–7.6 (1H, m), 7.65 (1H, s)

APCI-MS : 307 $[M+H-H_2O]^+$

Preparation 8

To a mixture of ethyl 2,3-dihydro-9-hydroxy-1-benzoxepin-4-carboxylate (1.17 g) and potassium carbonate (0.67 g) in N,N-dimethylformamide (11.7 ml) was added tert-butyl bromoacetate (0.74 ml) at ambient temperature. The reaction mixture was stirred overnight at the same temperature and partitioned between ethyl acetate and waster. The organic layer was washed successively with water and brine, dried over anhydrous magnesium sulfate, and evaporated in vacuo. The residue was triturated with petroleum ether to give a solid of ethyl 9-tert-butoxycarbonylmethoxy-2,3-dihydro-1-benzoxepin-4-carboxylate (1.63 g).

m; : 87–88° C.

IR (KBr) : 1745, 1697, 1637 $cm^{-1}$

NMR (DMSO-$d_6$, δ) : 1.35 (3H, t, J=7.1Hz, 1.47 (9H, s), 2.95–3.05 (2H, m), 4.27 (2H, q, J=7.1Hz), 4.3–4.4 (2H, m), 4.58 (2H, s), 6.82 (1H, dd, J=2.0, 7.8Hz), 6.92 (1H, dd, J=7.8, 7.8Hz), 7.00 (1H, dd, J=2.0, 7.8Hz), 7.57 (1H, s)

Preparation 9

To a mixture of sodium ethoxide (1.7 ml, 20% in ethanol) and dichlorobis(triphenylphosphine)palladium(II) (14 mg) in dichloromethane (7 ml) was added a mixture of ethyl 2,3-dihydro-9-iodo-1-benzoxepin-4-carboxylate (0.69 g) and ethyl formate (0.28 ml) at ambient temperature under nitrogen atmosphere. The reaction mixture was stirred at 40° C. for 3 hours and filtered off. The filtrate was partitioned between diethyl ether and 1N hydrochloric acid. The organic layer was washed successively with saturated aqueous sodium bicarbonate and brine, dried over anhydrous magnesium sulfate, and evaporated in vacuo. The residue was purified by medium pressure liquid chromatography (silica gel) using a mixture of ethyl acetate and n-hexane (1:19) as an eluent to give a solid of ethyl 2,3-dihydro-9-ethoxycarbonyl-1-benzoxepin-4-carboxylate (120 mg).

IR (Film) : 1726, 1709, 1631, 1585 $cm^{-1}$

NMR ($CDCl_3$, δ) : 1.35 (3H, t, J=7.1Hz,), 1.39 (3H, t, J=7.1Hz), 2.9–3.1 (2H, m), 4.2–4.45 (6H, m), 7.0–7.15 (1H, m), 7.4–7.5 (1H, m), 7.59 (1H, s), 7.6–7.7 (1H, m)

APCI-MS : 291 $[M+H]^+$

Preparation 10

To a mixture of ethyl 2,3-dihydro-9-hydroxy-1-benzoxepin-4-carboxylate (1.17 g) and triethylamine (0.14 ml) in dichloromethane (12 ml) was added dropwise trifluoromethanesulfonic anhydride (0.93 ml) under ice-sodium chloride cooling. The reaction mixture was stirred at 0° C. for 4 hours, poured into water, and adjusted to pH 10 with 20% aqueous potassium carbonate. The organic layer was washed with water, dried over anhydrous magnesium sulfate, and evaporated in vacuo. The residue was purified by medium pressure liquid chromatography (silica gel) using a mixture of ethyl acetate and n-hexane (1:30) to give a solid of ethyl 2,3-dihydro-9-trifluoromethanesulfonyloxy-1-benzoxepin-4-carboxylate (1.44 g).

mp : 52–53° C.

IR (KBr) : 1703 $cm^{-1}$

NMR ($CDCl_3$, δ) : 1.36 (3H, t, J=7.1Hz), 2.95–3.1 (2H, m), 4.29 (2H, q, j=7.1Hz), 4.3–4.4 (2H, m), 7.04 (1H, dd, J=7.9, 7.9Hz), 7.19 (1H, dd, J=1.7, 8.1Hz), 7.35 (1H, dd, J=1.7, 7.8Hz), 7.58 (1H, s)

APCI-MS : 367 $[M+H]^+$

Preparation 11

A mixture of zinc (69.2 mg, powder) and potassium cyanide (0.12 g) in N,N-dimethylformamide (10.5 ml) was stirred for 10 minutes under nitrogen atmosphere at ambient temperature and thereto was added successively ethyl 2,3-dihydro-9-trifluoromethanesulfonyloxy-1-benzoxepin-4-carboxylate (0.53 g), triethylamine (0.25 ml), and [1,1'-bis (diphenylphosphino)ferrocene]-dichloropalladium (0.12 g, complex with dichloromethane (1:1)). The reaction mixture was stirred at 60° C. for 2 hours. Thereto was added a mixture of ethyl acetate and water, basified by aqueous potassium carbonate, and filtered off. The organic layer was washed with brine, dried over anhydrous magnesium sulfate, and evaporated in vacuo. The residue was purified by medium pressure liquid chromatography (silica gel) using a mixture of ethyl acetate and n-hexane (1:9) to give a solid of ethyl 9-cyano-2,3-dihydro-1-benzoxepin-4-carboxylate (310 mg).

mp : 113–114° C.

IR (KBr) : 2233, 1699, 1635, 1583 $cm^{-1}$

NMR ($CDCl_3$, δ) : 1.36 (3H, t, J=7.1Hz), 2.95–3.1 (2H, m), 4.29 (2H, q, J6=7.1Hz), 2.95–3.1 (2H, m), 4.29 (2H, q, J=7.1Hz), 4.35–4.5 (2H, m), 7.0–7.15 (1H, m), 7.30 (1H, br s), 7.45–7.6 (3H, m)

APCI-MS : 244 $[M+H]^+$

Preparation 12

To a mixture of ethyl 2,3-dihydro-9-iodo-1-benzoxepin-4-carboxylate (5.62 g), potassium carbonate (9.03 g), and palladium(II) acetate (0.73 g) in aqueous N,N-dimethylformamide (48 ml, 67% v/v) was introduced carbon monoxide for 30 minutes. The reaction mixture was stirred for 2 days at ambient temperature in an atmosphere of carbon monoxide and partitioned between ethyl acetate and water. The aqueous layer was acidified with 1H hydrochloric acid and extracted with ethyl acetate. The organic layer was washed successively with saturated aqueous sodium thiosulfate and brine, dried over anhydrous magnesium sulfate, and evaporated in vacuo to give a solid of ethyl 9-carboxy-2,3-dihydro-1-benzoxepin-4-carboxylate (3.8 g).

mp : 132–134° C.

IR (KBr) : 1729, 1697, 1637 cm$^{-1}$

NMR (DMSO-$d_6$, δ) : 1.28 (3H, t, J=7.1Hz), 2.85–3.0 (2H, m), 4.21 (2H, q, J=7.1Hz), 4.25–4.35 (2H, m), 7.11 (1H, dd, J=7.6, 7.6Hz), 7.5–7.6 (1H, m), 7.55 (1H, s), 7.65 (1H, dd, J=1.6, 7.8Hz)

APCI-MS : 263 [M+H]$^+$

Preparation 13

To a mixture of ethyl 9-carboxy-2,3-dihydro-1-benzoxepin-4-carboxylate (0.52 g) and triethylamine (0.33 ml) in tetrahydrofuran (5.2 ml) was added dropwise isobutyl chloroformate (0.31 ml) below 5° C. under ice-sodium chloride cooling. The reaction mixture was stirred for 30 minutes at the same temperature. The resulting precipitate was filtered off and washed with cold tetrahydrofuran. The filtrate was added to a solution of sodium borohydride (75 mg) in aqueous tetrahydrofuran (10 ml, 90% v/v) at 0° C. The reaction mixture was stirred for 30 minutes at the ambient temperature and evaporated in vacuo. The residue was partitioned between ethyl acetate and water. The organic layer was washed with brine, dried over anhydrous magnesium sulfate, and evaporated in vacuo. The residue was purified by medium pressure liquid chromatography (silica gel) using a mixture of ethyl acetate and n-hexane (1:9) to give a solid of ethyl 2,3-dihydro-9-hydroxymethyl-1-benzoxepin-4-carboxylate (0.37 g).

mp : 75–76° C.

IR (KBr) : 3280, 1700 cm$^{-1}$

NMR (CDCl$_3$, δ) : 1.35 (3H, t, J=7.1Hz), 2.2–2.35 (1H, m), 2.95–3.05 (2H, m), 4.28 (2H, q, J=7.1Hz), 4.3–4.4 (2H, m), 4.71 (2H, d, J=5.9Hz), 6.95–7.1 (1H, m), 7.25–7.35 (2H, m), 7.55–7.65 (1H, m)

APCI-MS : 231 [M+H–H$_2$O]$^+$

Preparation 14

A mixture of ethyl 2,3-dihydro-9-hydroxymethyl-1-benzoxepin-4-carboxylate (0.45 g) and manganese (IV) oxide (4.5 g) was stirred under reflux for 1 hour and filtered off. The filtrate was evaporated in vacuo to give a solid of ethyl 2,3-dihydro-9-formyl-1-benzoxepin-4-carboxylate (0.43 g).

mp : 111–112° C.

IR (KBr) : 1701, 1670, 1631, 1577 cm$^{-1}$

NMR (CDCl$_3$, δ) : 1.37 (3H, t, J=7.1Hz), 2.95–3.1 (2H, m), 4.29 (2H, q, J=7.1Hz), 4.35–4.5 (2H, m), 7.05–7.2 (1H, m), 7.55–7.65 (2H, m), 7.75–7.85 (1H, m), 10.53 (1H, s)

APCI-MS ; 247 [M+H]$^+$

Preparation 15

A mixture of ethyl 2,3-dihydro-9-formyl-1-benzoxepin-4-carboxylate (0.40 g), hydroxylamine hydrochloride (0.14 g), and pyridine (0.16 ml) in ethanol (8 ml) was stirred under reflux for 40 minutes and evaporated in vacuo. The residue was partitioned between ethyl acetate and water. The organic layer was washed with brine, dried over anhydrous magnesium sulfate, and evaporated in vacuo. The residue was triturated with diisopropyl ether to give a solid of ethyl 2,3-dihydro-9-hydroxyiminomethyl-1-benxoepin-4-carboxylate (0.22 g).

mp : 145–146° C.

IR (KBr) : 3367, 1682, 1637, 1585 cm$^{-1}$

NMR (CDCl$_3$, δ) : 1.28 (3H, t, J=7.1Hz), 2.8–3.0 (2H, m), 4.21 (2H, q, J=7.1Hz), 4.25–4.4 (2H, m), 7.0–7.15 (1H, m), 7.53 (1H, s), 7.5–7.6 (1H, m), 7.65–7.75 (1H, m), 8.36 (1H, s), 11.33 (1H, br s)

APCI-MS : 262 [M+H]$^+$

Preparation 16

To a mixture of 9-carboxy-2,3-dihydro-1-benzoxepin-4-carboxylate (0.39 g), N,N-dimethylethylenediamine (0.163 ml), and 1-hydroxybenzotriaole hydrate (0.22 g) in dichloromethane (8 ml) was added 1-(3-dimethylamino-propyl)-3-ethylcarbodiimide hydrochloride (0.31 g). The reaction mixture was stirred for 4.5 hours at ambient temperature and evaporated in vacuo. The residue was partitioned between ethyl acetate and saturated aqueous sodium bicarbonate. The organic layer was washed successively with water and brine, dried over anhydrous magnesium sulfate, and evaporated in vacuo to give a solid of ethyl 2,3-dihydro-9-[2-(N,N-dimethylamino)-ethylaminocarbonyl]-1-benzoxepin-4-carboxylate (0.39 g), mp : 80–81° C.

IR (KBr) : 3359, 1701, 1658, 1631 cm$^{-1}$

NMR (DMSO-$d_6$, δ) : 1.28 (3H, t, J=7.1Hz), 2.20 (6H, s), 2.40 (2H, t, J=6.7Hz), 2.85–2.95 (2H, m), 3.25–3.4 (2H, m), 4.22 (2H, q, J=7.1Hz), 4.25–4.35 (2H, m), 7.13 (1H, dd, J=7.6, 7.6Hz), 7.5–7.7 (3H, m), 8.25–8.4 (1H, m)

APCI-MS : 333 [M+H]$^+$

Preparation 17

To a mixture of ethyl 2,3-dihydro-7-iodo-1-benzoxepin-4-carboxylate (0.69 g), triethylamine (1.12 ml), 1,3-bis(diphenylphosphino)propane (0.165 g), and palladium(II) acetate (90 mg) in N,N-dimethylformamide (6.4 ml) was introduced carbon monoxide for 30 minutes. The reaction mixture was stirred for 5 hours at 95° C. in an atmosphere of carbon monoxide and partitioned between ethyl acetate and water. The organic layer was washed successively with saturated aqueous sodium bicarbonate and brine, dried over anhydrous magnesium sulfate, and evaporated in vacuo. The residue was purified by medium pressure liquid chromatography (silica gel) using a mixture of ethyl acetate and n-hexane (1:4) to give a solid of ethyl 2,3-dihydro-7-methoxycarbonyl-1-benzoxepin-4-carboxylate (0.45 g).

mp : 79–81° C.

IR (KBr) : 1710, 1699, 1606 cm$^{-1}$

NMR (DMSO-$d_6$, δ) : 1.36 (3H, t, J=7.1Hz), 2.95–3.1 (2H, m), 3.91 (3H, s), 4.28 (2H, q, J=7.1Hz), 4.3–4.4 (2H, m), 7.00 (1H, d, J=8.5Hz), 7.62 (1h, s), 7.90 (1H, dd, J=2.2, 8.5Hz), 8.07 (1H, d, J=2.1Hz)

APCI-MS : 277 [M+H]$^+$

Preparation 18

A solution of ethyl 3-amino-2-(3-ethoxycarbonyl-propoxy)benzoate (8.93 g) in conc. hydrochloric acid (4.8 ml) was cooled in an ice bath. To this solution was added dropwise a solution of sodium nitrite (2.11 g) in water (5 ml) at 5° C. On the other hand, a solution of potassium xanthogenate (5.83 g) in water (7.6 ml) was heated at 50° C. To this solution was added dropwise the above solution of the diazonium salt at 50–55° C. The reaction mixture was cooled to room temperature and was extracted with ethyl acetate. After an additional extraction with ethyl acetate, the combined extracts were dried over magnesium sulfate and evaporated in vacuo to give the crude material, which was then dissolved in ethanol and 85% potassium hydroxide (9.10 g) was added to the solution. After the mixture was heated to reflux for 1.5 hours, it was cooled in an ice bath and acidified with conc. hydrochloric acid. The mixture was then extracted with ethyl acetate (x 3). The combined extracts were dried over magnesium sulfate and evaporated in vacuo to give 3-mercapto-2-(3-carboxypropoxy)benzoic acid (7.08 g) as yellow crystals.

A mixture of the mercaptobenzoic acid (7.08 g), potassium carbonate (4.26 g) and iodomethane (6.44 g) in acetone (70 ml) was heated to reflux under nitrogen atmosphere for 4 hours. Acetone was evaporated in vacuo and the residue was partitioned between water and ethyl acetate. After an additional extraction with ethyl acetate, the combined extracts were washed with water, dried over magnesium sulfate, and evaporated in vacuo to give 1.64 g of the crude material. The aqueous layer was acidified with 1N hydrochroric acid. The precipitates were collected by filtration, washed with water, and dried to give 5.22 g of rude material. The combined crude material (6.896 g) was purified by column chromatography on silica gel using a mixture of chloroform and methanol (10:1) to give light brown crystals of 3-methylthio-2-(3-carboxypropoxy)benzoic acid (5.21 g).

mp : 162–164° C. (ethyl acetate)
IR (Nujol) : 1695, 1585, 1560 cm$^{-1}$
NMR (DMSO-d$_6$, δ) : 1.87–2.00 (2H, m), 2.41 (3H, s), 2.48–2.51 (2H, m), 3.95 (2H, t, J=6.2Hz), 7.19 (1H, t, J=7.7Hz), 7.35 (1H, dd, J=7.7, 1.7Hz), 7.44 (1H, dd, J=7.7, 1.7Hz)

Preparation 19

A solution of 3-methylthio-2-(3-carboxypropoxy)-benzoic acid (4.80 g) and conc. sulfuric acid (1.0 ml) in ethanol (96 ml) was heated to reflux for 19 hours. Ethanol was evaporated in vacuo, and the residue was partitioned between 1N sodium hydroxide and ethyl acetate. After an additional extraction with ethyl acetate, the combined extracts were washed with brine, dried over magnesium sulfate, and evaporated in vacuo. The crude material was purified by column chromatography on silica gel using a mixture of n-hexane and ethyl acetate (10:1) to give ethyl 3-methylthio-2-(3-ethoxycarbonylpropoxy)-benzoate (5.20 g) as an oil.

IR (Film) : 2925, 1720, 1585, 1560 cm$^{-1}$
NMR (CDCl$_3$, δ) : 1.27 (3H, t, J=7.1Hz), 1.39 (3H, t, J=7.1Hz, 2.07–2.22 (2H, m), 2.42 (3H, s), 2.64 (2H, t, J=7.5Hz), 4.05 (2H, t, J=6.1Hz), 4.16 (2H, q, J=7.1Hz), 4.37 (2H, q, J=7.1Hz), 7.13 (1H, t, J=7.7Hz), 7.28 (1H, dd, J=7.7, 1.7Hz), 7.57 (1H, dd, J=7.7, 1.7Hz)
APCI-MS : 327 [M+H]$^+$ Preparation 20

To a solution of ethyl 3-methylthio-2-(3-ethoxycarbonylpropoxy)benzoate (3.83 g) in a mixture of ethanol (34 μl) and N,N-dimethylformamide (40 ml) was added 60% sodium hydroxide (1.03 mg) at 5° C. After the mixture was allowed to stir at room temperature for 15.5 hours, it was poured into ice-water and extracted with ethyl acetate (x 3). The combined extracts were washed with water (x 2) and brine, dried over magnesium sulfate, and evaporated in vacuo. The crude product was purified by column chromatography on silica gel using a mixture of n-hexane and ethyl acetate (20:1) to give ethyl 9-methylthio-5-oxo-2,3,4,5-tetrahydro-1-benzoxepin-4-carboxylate (2.61 g, colorless crystals).

mp : 89–90° C. (ethyl acetate—diisopropyl ether)
IR (Nujol) : 1740, 1675, 1640, 1590, 1560 cm$^{-1}$
NMR (CDCl$_6$, δ) : 1.23 (3H, t, J=7.1Hz), 2.45 (3H, s), 2.52–2.61 (2H, m), 4.02–4.52 (4H, m), 4.54–4.61 (1H, m), 7.12 (1H, t, J=7.7Hz), 7.29 (1H, dd, J=7.7, 1.7Hz), 7.58 (1H, dd, J=7.7, 1.7Hz)

Anal. Calcd. for C$_{14}$H$_{16}$O$_4$S : C 59.98, H 5.75 Found : C 59.73, H 5.74

Preparation 21

The following compounds were obtained according to a similar manner to that of Preparation 20.

(1) Ethyl 2,3,4,5-tetrahydro-9-hydroxy-5-oxo-1-benzoxepin-4-carboxylate
IR (Film) : 3400, 1715, 1665, 1575 cm$^{-1}$
NMR (CDCl$_3$, δ) : 1.15–1.45 (3H, m), 2.35–2.75 (2H, m), 4.0–4.6 (6H, m), 5.85–6.05 (1H, m), 7.05–7.2 (1H, m), 6.95–7.45 (3H, m)
APCI-MS : 251 [M+H]$^+$ (2) Ethyl 2,3,4,5-tetrahydro-5-oxo-9-iodo-1-benzoxepin-4-carboxylate
IR (Film) : 1730, 1675, 1580 cm$^{-1}$
NMR (CDCl$_3$, δ) : 1.22 (3H, t, J=7.1Hz), 2.45–2.75 (2H, m), 4.0–4.45 (4H, m), 4.45–4.65 (1H, m), 6.89 (1H, dd, J=7.8, 7.8Hz), 7.77 (1H, dd, J=1.7, 7.8Hz), 7.95 (1H, dd, J=1.7, 7.8Hz)
APCI-MS : 361 [M+H]$^+$ (3) Ethyl 7-iodo-4oxo-2,3,4,5-tetrahydro-1-benzoxepin-4-carboxylate
mp : 82–85° C.
IR (KBr) : 1743, 1683 cm$^{-1}$
NMR (CDCl$_3$, δ) : 1.2–1.4 (3H, m), 2.55–2.75 (2H, m), 4.1–4.5 (4H, m), 6.7–7.1 (2H, m), 7.55–8.0 (1H, m), 8.1–8.3 (1H, m)
APCI-MS : 361 [M+H]$^+$ Preparation 22

To a suspension of ethyl 9-methylthio-5-oxo-2,3,4,5-tetrahydro-1-benzoxepin-4-carboxylate (2.48 g) in ethanol (25 ml) was added sodium borohydride (248 mg) at 5° C. After the mixture was stirred at the same temperature for 1 hour, it was warmed up to room temperature and stirred for 30 minutes. The reaction mixture was cooled in an ice bath, quenched with 1N hydrochloric acid, and partitioned between brine and ethyl acetate. After an additional extraction with ethyl acetate, the combined extracts were washed with brine, dried over magnesium sulfate, and evaporated in vacuo to give an oil, which was purified by column chromatography on silica gel using a mixture of n-hexane and ethyl acetate (5:1) to afford cis and trans mixture of ethyl 5-hydroxy-9-methylthio-2,3,4,5-tetrahydro-1-benzoxepin-4-carboxylate (1.66 g) as an oil.

IR (Film): 3430, 1718, 1560 cm$^{-1}$
NMR (CDCl$_3$, δ): 1.19–1.26 (3H, m), 2.17–2.30 (2H, m), 2.40 (3H, s), 2.78–3.04 (2H, m), 3.79–4.37 (4H, m), 5.16–5.20 (1H, m), 7.02–7.16 (3H, m)

Preparation 23

The following compounds were obtained according to a similar manner to that of Preparation 22.

(1) Ethyl 2,3,4,5-tetrahydro-5,9-dihydroxy-1-benzoxepin-4-carboxylate
IR (Film): 3300, 1700, 1585 cm$^{-1}$
NMR (CDCl$_3$, δ): 1.15–1.35 (3H, m), 2.1–3.1 (3H, m), 3.8–4.4 (5H, m), 5.1–5.2 (1H, m), 5.8–6.0 (1H, m), 6.8–7.05 (3H, m)
APCI-MS: 235 [M+H-H$_2$O]$^+$ (2) Ethyl 2,3,4,5-tetrahydro-5-hydroxy-9-iodo-1-benzoxepin-4-carboxylate
IR (Film): 3470, 1715 cm$^{-1}$
NMR (CDCl$_3$, δ): 1.1–1.3 (3H, m), 2.1–2.9 (2H, m), 2.95–3.1 (1H, m), 3.75–4.35 (5H, m), 5.1–5.25 (1H, m), 6.75–6.9 (1H, m), 7.3–7.55 (1H, m), 7.65–7.75 (1H, m)
APCI-MS: 362 [M+H]$^+$, 345 [M+H-H$_2$O]$^+$ (3) Ethyl 7-iodo-5-hydroxy-2,3,4,5-tetrahydro-1-benzoxepin-4-carboxylate IR (Film): 3470 (br), 1739, 1724, 1709 cm$^{-1}$ NMR (CDCl$_3$, δ): 1.15–1.35 (3H, m), 2.1–2.45 (1H, m), 2.5–3.15 (1H, m), 3.3–3.45 (1H, m), 4.0–4.35 (4H, m), 5.05–5.25 (1H, m), 6.7–6.8 (1H, m), 7.4–7.45 (1H, m), 7.65–7.9 (1H, m)

APCI-MS: 345 [M+H-H$_2$O]$^+$

Preparation 24

A solution of p-toluenesulfonic acid monohydrate (109 mg) and ethyl 5-hydroxy-9-methylthio-2,3,4,5-tetrahydro-1-benzoxepin-4-carboxylate (cis and trans mixture, 1.62 g) in toluene (32 ml) was heated to reflux for 1.5 hours. The reaction mixture was diluted with ethyl acetate, washed successively with saturated aqueous sodium hydrogen carbonate and brine, dried over magnesium sulfate, and evaporated in vacuo to give 1.60 g of crude product, which was purified by column chromatography on silica gel using a mixture of n-hexane and ethyl acetate (30:1) to afford ethyl 2,3-dihydro-9-methylthio-1-benzoxepin-4-carboxylate (1.30 g, colorless needles).

mp: 54–55° C. (n-hexane—diisopropyl ether)

IR (Nujol): 1690 cm$^{-1}$

NMR (CDCl$_3$, δ): 1.35 (3H, t, J=7.1 Hz), 2.43 (3H, s), 3.00 (2H, t, J=5.0 Hz), 4.27 (2H, q, J=7.1 Hz), 4.37 (2H, t, J=5.0 Hz), 6.98–7.17 (3H, m), 7.56 (1H, s)

Anal. Calcd. for C$_{14}$H$_{16}$O$_3$S: C 63.61, H 6.10 Found: C 63.74, H 6.13

Preparation 25

In following compound was obtained according to a similar manner to that of Preparation 24.

(1) Ethyl 2,3-dihydro-9-hydroxy-1-benzoxepin-4-carboxylate mp: 85–86° C.

IR (Nujol): 3360, 1680, 1615 cm$^{-1}$

NMR (CDCl$_3$, δ): 1.35 (3H, t, J=7.1 Hz), 2.95–3.1 (2H, m), 4.28 (2H, q, J=7.1 Hz), 4.3–4.4 (2H, m), 5.93 (1H, s), 6.8–7.0 (3H, m), 7.57 (1H, br s)

APCI-MS: 235 [M+H]$^+$ (2) Ethyl 2,3-dihydro-9-iodo-1-benzoxepin-4-carboxylate

IR (Film): 1695, 1630 cm$^{-1}$

NMR (CDCl$_3$, δ): 1.35 (3H, t, J=7.1 Hz), 2.95–3.05 (2H, m), 4.28 (2H, q, J=7.1 Hz), 4.25–4.4 (2H, m), 6.76 (1H, dd, J=7.7, 7.7 Hz), 7.32 (1H, dd, J=1.5, 7.7 Hz), 7.51 (1H, s), 7.75 (1H, dd, J=1.5, 7.7 Hz)

APCI-MS: 345 [M+H]$^+$ (3) Ethyl 2,3-dihydro-7-iodo-1-benzoxepin-4-carboxylate mp: 70–72° C.

IR (KBr): 1703, 1633 cm$^{-1}$

NMR (CDCl$_3$, δ): 1.35 (3H, t, J=7.1 Hz), 2.9–3.05 (2H, m), 4.14–4.35 (4H, m), 6.73 (1H, dd, J=8.6 Hz), 7.45 (1H, s), 7.48 (1H, dd, J=2.2, 8.6 Hz), 7.64 (1H, d, J=2.2 Hz)

APCI-MS: 345 [M+H]$^+$

Preparation 26

A mixture of ethyl 9-amino-2,3-dihydro-1-benzoxepin-4-carboxylate (0.35 g), 4-chlorobutyryl chloride (0.202 ml) and pyridine (0.146 ml) in dichloromethane (3.5 ml) was stirred at room temperature for 2 hours. The reaction mixture was diluted with ethyl acetate, and the solution was washed successively with 1N hydrochloric acid, saturated aqueous sodium bicarbonate solution and brine, dried over magnesium sulfate, and evaporated in vacuo. The residue was purified by column chromatography on silica gel using a mixture of n-hexane and ethyl acetate (3:1) as an eluent to give colorless crystals of ethyl 9-(4-chlorobutyryl)amino-2,3-dihydro-1-benzoxepin-4-carboxylate (0.48 g).

mp: 98–99° C.

IR (KBr): 1695, 1662, 1635 cm$^{-1}$

NMR (CDCl$_3$, δ): 1.35 (3H, t, J=7.1 Hz), 2.1–2.35 (2H, m), 2.62 (2H, t, J=7.1 Hz), 2.95–3.10 (2H, m), 3.68 (2H, t, J=6.2 Hz), 4.28 (2H, q, J=7.1 Hz), 4.35–4.45 (2H, m), 6.95–7.10 (2H, m), 7.57 (1H, s), 7.99 (1H, br s), 8.30–8.50 (1H, m)

APCI-MS: 338 [M+H]$^+$

Preparation 27

To a solution of ethyl 9-(4-chloro-1-oxobutylamino)-2,3-dihydro-1-benzoxepin-4-carboxylate (0.44 g) in N,N-dimethylformamide (4.4 ml) was added sodium hydride (0.17 g, 60%) at ambient temperature. The reaction mixture was stirred for 1.5 hours at the same temperature and partitioned between ethyl acetate and 1N hydrochloric acid. The organic layer was washed successively with water and brine, dried over anhydrous magnesium sulfate, and evaporated in vacuo. The residue was purified by medium pressure liquid chromatography (silica gel) using a mixture of ethyl acetate and n-hexane (1:4~1:1) to give a solid of ethyl 2,3-dihydro-9-(2-oxo-1-pyrrolidinyl)-1-benzoxepin-4-carboxylate (0.21 g).

mp: 64–66° C.

IR (KBr): 1699, 1676, 1633 cm$^{-1}$

NMR (CDCl$_3$, δ): 1.35 (3H, t, J=7.1 Hz), 2.1–2.3 (2H, m), 2.5–2.65 (2H, m), 2.9–3.05 (2H, m), 3.7–3.85 (2H, m), 4.2–4.35 (2H, m), 6.95–7.1 (1H, m), 7.15–7.35 (2H, m), 7.59 (1H, s)

APCI-MS: 302 [M+H]$^+$

Preparation 28

A mixture of ethyl 3-benzyloxy-2-(3-ethoxycarbonylpropyloxy)benzoate (2.5 g) and palladium on charcoal (0.25 g) in ethanol (12.5 ml) was hydrogenated under hydrogen atmosphere. The catalyst was filtered off. The filtrate was evaporated in vacuo. The residue was purified by silica gel column chromatography using a mixture of ethyl acetate and n-hexane (1:3) to give colorless oil of ethyl 3-hydroxy-2-(3-ethoxycarbonylpropyloxy)benzoate (1.86 g).

IR (Film): 3380, 1710, 1585 cm$^{-1}$

NMR (CDCl$_3$, δ): 1.27 (3H, t, J=7.1 Hz), 1.39 (3H, t, J=7.1 Hz), 2.1–2.25 (2H, m), 2.55–2.7 (2H, m), 4.06 (2H, t, J=5.8 Hz), 4.19 (2H, q, J=7.1 Hz), 4.36 (2H, q, J=7.1 Hz), 5.10 (2H, s), 7.0–7.1 (1H, m), 7.14 (1H, dd, J=1.9, 8.0 Hz), 7.36 (1H, dd, J=1.9, 7.7 Hz)

Preparation 29

To a mixture of ethyl 3-hydroxy-2-(3-ethoxycarbonylpropyloxy)benzoate (1.50 g) and imidazole (0.52 g) in N,N-dimethylformamide (7.5 ml) was added tert-butyldimethylsilyl chloride (0.82 g) at ambient temperature. The reaction mixture was stirred for 2.5 hours at the same temperature and partitioned between ethyl acetate and water. The organic layer was washed with brine, dried over anhydrous magnesium sulfate, and evaporated in vacuo. The residue was purified by medium pressure liquid chromatography (silica gel) using a mixture of ethyl acetate and n-hexane (1:9) to give colorless oil of ethyl 3-tert-butyldimethylsilyloxy)-2-(3-ethoxycarbonylpropyloxy)benzoate (1.97 g).

IR (Film): 1715, 1570 cm$^{-1}$

NMR (CDCl$_3$, δ): 0.20 (6H, s), 1.01 (9H, s), 1.26 (3H, t, J=7.1 Hz), 1.38 (3H, t, J=7.1 Hz), 2.0–2.2 (2H, m), 2.45–2.6 (2H, m), 4.05 (2H, t, J=6.5 Hz), 4.14 (2H, q, J=7.1 Hz), 4.36 (2H, q, J=7.1 Hz), 6.95–7.05 (2H, m), 7.25–7.35 (1H, m)

Preparation 30

70% m-Chloroperbenzoic acid (35.1 g) was added to a solution of ethyl 2,3-dihydro-9-methylthio-1-benzoxepin-4-carboxylate (15.0 g) in dichloromethane (300 ml) at 5° C.

The mixture was stirred at 5–15° C. for 2 hours, and poured into a mixture of aqueous sodium thiosulfate (20 g/200 ml) and aqueous saturated sodium bicarbonate (200 ml). The organic layer was separated, and the aqueous layer was extracted with dichloromethane (200 ml). The extracts were combined and washed successively with saturated aqueous sodium bicarbonate and brine, dried over anhydrous magnesium sulfate, and concentrated under reduced pressure. The residue was purified by column chromatography on silica gel using a mixture of chloroform and ethyl acetate (20:1) to give 14.6 g of colorless crystals, which were then recrystallized from a mixture of ethyl acetate and diisopropyl ether to give ethyl 2,3-dihydro-9-methanesulfonyl-1-benzoxepin-4-carboxylate (12.72 g). The mother liquid was concentrated to give additional amount of ethyl 2,3-dihydro-9-methanesulfonyl-1-benzoxepin-4-carboxylate (1.09 g).

mp: 104–105° C.

IR (Nujol): 1700, 1640, 1595, 1570, 1300, 1140 $cm^{-1}$

NMR ($CDCl_3$, δ): 1.36 (3H, t, J=7.1 Hz), 3.08 (2H, dt, J=1.2, 4.8 Hz), 3.26 (3H, s), 4.30 (2H, q, J=7.1 Hz), 4.45 (2H, t, J=4.8 Hz), 7.20 (1H, t, J=7.8 Hz), 7.61 (12H, s), 7.63 (1H, dd, J=1.7, 7.8 Hz), 7.96 (1H, dd, J=1.7, 7.8 Hz)

ESI-MS: 297 $[M+H]^+$

Preparation 31

The following compound was obtained according to a similar manner to that of Preparation 26.

Ethyl 2,3-dihydro-9-ethoxycarbonylamino-1-benzoxepin-4-carboxylate mp: 76.5–78° C. (ethyl acetate)

IR (Nujol): 3410, 1729, 1702, 1633 $cm^{-1}$

NMR (DMSO-$d_6$, δ): 1.26 (6H, q, J=7.1 Hz), 2.8–2.95 (2H, m), 4.01–4.39 (6H, m), 7.01 (1H, t, J=7.9 Hz), 7.17 (1H, dd, J=1.6, 7.9 Hz), 7.50 (1H, s), 7.74 (1H, dd, J=1.6, 7.9 Hz), 8.66 (1H, s)

APCI-MS: 306 $[M+H]^+$

Preparation 32

A solution of sodium nitrate (800 mg) in water (3 ml) was added to a suspension of ethyl 9-amino-2,3-dihydro-1-benzoxepin-4-carboxylate (2.56 g) in a mixture of conc. hydrochloric acid (18 ml) and acetic acid (12.5 ml) under sodium chloride—ice bath cooling, and the mixture was stirred at the same temperature for 50 minutes. On the other hand, sulfur dioxide gas was introduced to acetic acid (40 ml) at room temperature, and the solution was cooled to −10° C. under stirring. To this was added copper(II) chloride (545 mg), followed by addition of the diazonium salt solution dropwise. After the addition was completed, the mixture was stirred at room temperature for 16 hours. The reaction mixture was poured into ice-water, and extracted with ethyl acetate (×3). The combined extracts were successively washed with water, saturated aqueous sodium bicarbonate and brine, dried over anhydrous magnesium sulfate, and concentrated under reduced pressure to give ethyl 9-chlorosulfonyl-2,3-dihydro-1-benzoxepin-4-carboxylate (0.72 g) as an oil.

NMR ($CDCl_3$, δ): 1.37 (3H, t, J=7.1 Hz), 3.13 (2H, dt, J=1.3, 4.8 Hz), 4.30 (2H, q, J=7.1 Hz), 4.51 (2H, t, J=4.8 Hz), 7.20 (1H, t, J=7.9 Hz), 7.60 (1H, s), 7.71 (1H, dd, J=1.6, 7.8 Hz), 7.94 (1H, dd, J=1.6, 7.8 Hz)

Preparation 33

A solution of ethyl 9-chlorosulfonyl-2,3-dihydro-1-benzoxepin-4-carboxylate (0.50 g) in tetrahydrofuran (12 ml) was cooled in an ice bath. To this solution was added dropwise morphorine (0.69 ml) at 5° C. The reaction mixture was stirred at 5° C. for 40 minutes and partitioned between ethyl acetate and water. The aqueous layer was extracted twice with ethyl acetate. The combined organic layer was dried over anhydrous magnesium sulfate and evaporated in vacuo. The residue was purified by column chromatography on silica gel using a mixture of n-hexane and ethyl acetate (1:1) to give ethyl 2,3-dihydro-9-morphorinosulfonyl-1-benzoxepin-4-carboxylate (0.54 g).

mp: 123–124° C. (ethyl acetate)

IR (Nujol): 1707, 1639 $cm^{-1}$

NMR (DMSO-$d_6$, δ): 1.28 (3H, t, J=7.1 Hz), 2.85–3.00 (2H, m), 3.05–3.20 (4H, m), 3.55–3.70 (4H, m), 4.22 (2H, q, J=7.1 Hz), 4.30–4.45 (2H, m), 7.23 (1H, t, J=7.8 Hz), 7.58 (1H, s), 7.70–7.95 (2H, m)

APCI-MS: 368 $[M+H]^+$

Preparation 34

The following compounds were obtained according to a similar manner to that of Preparation 33.

(1) Ethyl 9-aminosulfonyl-2,3-dihydro-1-benzoxepin-4-carboxylate mp: 197–198° C. (95% ethanol)

IR (Nujol): 3300, 3230, 1685, 1630, 1565 $cm^{-1}$

NMR (DMSO-$d_6$, δ): 1.29 (3H, t, J=7.1 Hz), 2.94 (2H, t, J=4.6 Hz), 4.22 (2H, q, J=7.1 Hz), 4.39 (2H, t, J=4.6 Hz), 7.18 (1H, t, J=7.7 Hz), 7.24 (2H, s), 7.77 (2H, d, J=7.7 Hz)

(2) Ethyl 2,3-dihydro-9-methylaminosulfonyl-1-benzoxepin-4-carboxylate mp: 137–139° C. (ethyl acetate)

IR (Nujol): 3318, 1705 $cm^{-1}$

NMR (DMSO-$d_6$, δ): 1.28 (3H, t, J=7.1 Hz), 2.44 (3H, d, J=4.5 Hz), 2.90–3.00 (2H, m), 4.22 (2H, q, J=7.1 Hz), 4.35–4.45 (2H, m), 7.21 (1H, t, J=7.7 Hz), 7.58 (1H, s), 7.7–7.9 (2H, m)

APCI-MS: 312 $[M+H]^+$

Preparation 35

A mixture of ethyl 2,3-dihydro-9-iodo-1-benzoxepin-4-carboxylate (1.00 g), trifluoroacetic acid, sodium salt (1.58 g), and copper(I) iodide (1.11 g) in 1-methyl-2-pyrrolidinone (10 ml) was stirred at 160° C. under nitrogen atmosphere for 6 hours and partitioned between ethyl acetate and 1N hydrochloric acid. The aqueous layer was extracted twice with ethyl acetate. The combined organic layer was washed successively with saturated aqueous sodium bicarbonate and brine, dried over anhydrous magnesium sulfate, and evaporated in vacuo. The residue was purified by column chromatography on silica gel using a mixture of n-hexane and ethyl acetate (4:1) to give ethyl 2,3-dihydro-9-trifluoromethyl-1-benzoxepin-4-carboxylate (0.93 g).

mp: 57–59° C. (ethyl acetate)

IR (Nujol): 3334, 3140, 1702, 1652, 1590 $cm^{-1}$

NMR (DMSO-$d_6$, δ): 1.29 (3H, t, J=7.1 Hz), 2.85–3.10 (2H, m), 4.23 (2H, q, J=7.1 Hz), 4.25–4.45 (2H, m), 7.23 (1H, t, J=7.8 Hz), 7.58 (1H, s), 7.66 (1H, d, J=7.8 Hz), 7.84 (1H, d, J=7.8 Hz)

APCI-MS: 287 $[M+H]^+$

Preparation 36

To a mixture of ethyl 9-amino-2,3-dihydro-1-benzoxepin-4-carboxylate (1.0 g) and triethylamine (4.18 ml) in tetrahydrofuran (10 ml) was added dimethylsulfamoyl chloride (2.30 ml) at 5° C. The reaction mixture was stirred overnight at ambient temperature and partitioned between ethyl acetate and 1N hydrochloric acid. The organic layer was washed successively with saturated aqueous sodium bicarbonate and brine, dried over anhydrous magnesium sulfate, and evaporated in vacuo. The residue was purified by column chromatography on silica gel using a mixture of n-hexane and ethyl acetate (4:1) to give ethyl 2,3-dihydro-9-dimethylsulfamoylamino-1-benzoxepin-4-carboxylate (0.89 g).

mp: 93–96° C. (ethyl acetate)

IR (Nujol): 3249, 1711 cm$^{-1}$

NMR (DMSO-d$_6$, δ): 1.27 (3H, t, J=7.1 Hz), 2.67 (3H, s), 2.75 (3H, s), 2.85–3.00 (2H, m), 4.10–4.35 (4H, m), 7.01 (1H, t, J=7.8 Hz), 7.27 (1H, d, J=7.8 Hz), 7.38 (1H, d, J=7.8 Hz), 7.51 (1H, s), 9.11 (1H, s)

APCI-MS: 341 [M+H]$^+$

Preparation 37

The following compound was obtained according to a similar manner to that of Preparation 36.

Ethyl 2,3-dihydro-9-sulfamoylamino-1-benzoxepin-4-carboxylate mp: 135–137° C.

IR (Nujol): 3348, 3261, 1699 cm$^{-1}$

NMR (DMSO-d$_6$, δ): 1.28 (3H, t, J=7.1 Hz), 2.75–3.00 (2H, m), 4.10–4.40 (4H, m), 7.02 (1H, t, J=7.8 Hz), 7.10 (2H, br s), 7.19 (1H, dd, J=7.8, 1.6 Hz), 7.42 (1H, dd, J=7.8, 1.6 Hz), 7.47 (1H, s), 8.32 (1H, s)

APCI-MS: 313 [M+H]$^+$

Preparation 38

A solution of ethyl 9-carboxy-2,3-dihydro-1-benzoxepin-4-carboxylate (1.0 g) in tetrahydrofuran (10 ml) was cooled in an ice bath. To this solution was added 1-hydroxybenzotriazole hydrate (0.57 g) and 1-(3-dimethylaminopropyl)-3-ethylcarboxiimide hydrochloride (0.80 g). Thereto aqueous ammonia (0.28 ml) was added dropwise at 5° C. The reaction mixture was stirred for 7 hours at ambient temperature and partitioned between ethyl acetate and 1N hydrochloric acid. The aqueous layer was extracted twice with ethyl acetate. The combined organic layer was washed successively with saturated aqueous sodium bicarbonate and brine, dried over anhydrous magnesium sulfate and evaporated in vacuo. The residue was purified by column chromatography on silica gel using a mixture of chloroform and methanol (9:1) to give ethyl 2,3-dihydro-9-carbamoyl-1-benzoxepin-4-carboxylate (0.31 g).

mp: 120–125° C. (ethyl acetate)

IR (Nujol): 3450, 3176, 1703, 1666 cm$^{-1}$

NMR (DMSO-d$_6$, δ): 1.28 (3H, t, J=7.1 Hz), 2.80–3.05 (2H, m), 4.24 (2H, q, J=7.1 Hz), 4.25–4.45 (2H, m), 7.11 (1H, t, J=7.6 Hz), 7.40–7.90 (5H, m)

APCI-MS: 262 [M+H]$^+$

EXAMPLE 1

To a mixture of ethyl 2,3-dihydro-9-ethoxycarbonyl-1-benzoxepin-4-carboxylate (0.10 g) and guanidine hydrochloride (0.33 g) in N,N-dimethylformamide (2 ml) was added 28% sodium methoxide in methanol (0.66 ml) at room temperature. After the mixture was stirred at room temperature overnight, it was purified by column chromatography on silica gel using a mixture of chloroform and methanol (30:1 to 4:1). The fractions containing objective compound was collected and evaporated in vacuo. The residue was treated with methanol and 4N hydrogen chloride in 1,4-dioxane, and the solvent was evaporated in vacuo. The residue was triturated with ethanol to give (2,3-dihydro-9-guanidinocarbonyl-1-benzoxepin-4-carbonyl)guanidine dihydrochloride (46 mg).

mp: 284–288° C. (dec.) (ethanol)

IR (KBr): 1701, 1682, 1630 cm$^{-1}$

NMR (DMSO-d$_6$, δ): 2.85–3.05 (2H, m), 4.35–4.55 (2H, m), 7.2–7.35 (1H, m), 7.30 (1H, br s), 7.79–7.9 (2H, m), 7.96 (1H, s), 8.4–8.9 (8H, m), 11.6 (1H, br s), 12.4 (1H, br s)

APCI-MS: 307 [M+H]$^+$

Anal. Calcd. for $C_{14}H_{19}N_3O_5S$: C 49.26, H 5.61, N 12.31 Found: C 49.64, H 5.63, N 12.26

EXAMPLE 2

The following example compounds were obtained according to a similar manner to that of Example 1.

(1) [9-[(E)-(2-Carboxyvinyl)]-2,3-dihydro-2,3-dihydro-1-benzoxepin-4-carbonyl]guanidine hydrochloride mp: 279–281° C. (dec.) (diisopropyl ether—methanol)

IR (KBr): 1689, 1631, 1606 cm$^{-1}$

NMR (DMSO-d$_6$, δ): 2.27 (3H, s), 2.44 (3H, s), 2.89 (2H, t, J=4.6 Hz), 4.22 (2H, t, J=4.6 Hz), 6.90 (1H, d, J=8.2 Hz), 7.15 (1H, dd, J=1.8, 8.2 Hz), 7.30 (1H, br s), 7.38 (1H, s), 8.37 (4H, br s), 10.98 (1H, br s)

APCI-MS: 302 [M+H]$^+$

Anal. Calcd. for $C_{15}H_{16}ClN_3O_4 \cdot 1.2H_2O$: C 50.13, H 5.16, N 11.69 Found: C 50.39, H 5.25, N 11.15

(2) [2,3-Dihydro-9-[(E)-(2-guanidinocarbonylvinyl)]-1-benzoxepin-4-carbonyl]guanidine dihydrochloride mp: >300° C. (diisopropyl ether—methanol)

IR (KBr): 1700, 1685, 1630, 1614 cm$^{-1}$

NMR (DMSO-d$_6$, δ): 2.85–3.04 (2H, m), 4.3–4.5 (2H, m), 6.88 (1H, d, J=16.0 Hz), 7.15–7.3 (1H, m), 7.65–7.8 (1H, m), 7.89 (1H, s), 8.05 (1H, d, J=16.0 Hz), 8.2–8.85 (8H, m), 12.07 (2H, br s)

APCI-MS: 343 [M+H]$^+$

Anal. Calcd. for $C_{16}H_{20}Cl_2N_6O_4 \cdot H_2O$: C 44.35, H 5.12, N 19.40 Found: C 44.45, H 4.73, H 19.07

(3) [2,3-Dihydro-9-(2-hydroxymethylphenyl)-1-benzoxepin-4-carbonyl]guanidine hydrochloride mp: 244–246° C. (diisopropyl ether—methanol)

IR (KBr): 3371, 1701, 1624, 1574 cm$^{-1}$

NMR (DMSO-d$_6$, δ): 2.75–2.95 (2H, m), 4.0–4.4 (4H, m), 5.04 (1H, br s), 7.05–7.45 (5H, m), 7.5–7.7 (2H, m), 7.89 (1H, s), 8.25–8.85 (4H, m), 11.81 (1H, br s)

APCI-MS: 338 [M+H]$^+$

Anal Calcd. for $C_{19}H_{20}ClN_3O_3 \cdot 0.5H_2O$: C 59.61, H 5.53, N 10.98 Found: C 59.85, H 5.51, N 10.90

(4) [9-(2,5-Dichloro-3-thienyl)-2,3-dihydro-1-benzoxepin-4-carbonyl]guanidine hydrochloride mp: 240–243° C. (dec.) (diisopropyl ether—methanol)

IR (KBr): 1712, 1625, 1581 cm$^{-1}$

NMR (DMSO-d$_6$, δ): 2.8–3.0 (2H, m), 4.2–4.4 (2H, m), 7.1–7.25 (1H, m), 7.20 (1H, s), 7.37 (1H, dd, J=1.7, 7.5 Hz), 7.66 (1H, dd, J=1.7, 6.8 Hz), 7.87 (1H, s), 8.25–8.8 (4H, m), 11.83 (1H, br s)

APCI-MS: 382 [M+H]$^+$

Anal. Calcd. for $C_{16}H_{14}Cl_3N_3O_2S$: C 45.90, H 3.37, N 10.04 Found: C 45.60, H 3.39, N 9.91

(5) {2,3-Dihydro-9-[2-(N,N-dimethylamino)ethylaminocarbonyl]-1-benzoxepin-4-carbonyl}guanidine dihydrochloride mp: 257–259° C. (dec.) (diisopropyl ether—methanol)

IR (KBr): 3340 (br), 3126, 2698, 1690 (br), 1635 cm$^{-1}$

NMR (DMSO-d$_6$, δ): 2.82 (6H, s), 2.9–3.05 (2H, m), 3.2–3.3 (2H, m), 3.55–3.75 (2H, m), 4.3–4.45 (2H, m), 7.1–7.25 (1H, m), 7.65–7.8 (2H, m), 7.95 (1H, s), 8.4–8.85 (5H, m), 10.30 (1H, br s), 12.07 (1H, br s)

APCI-MS: 346 [M+H]$^+$

Anal Calcd. for $C_{17}H_{25}Cl_2N_5O_3 \cdot 2.3H_2O$: C 44.41, H 6.49, N 15.23 Found: C 44.66, H 6.32, N 14.97

(6) [2,3-Dihydro-9-(2-oxo-1-pyrrolidinyl)-1-benzoxepin-4-carbonyl]guanidine hydrochloride mp: 240–251° C. (dec.) (diisopropyl ether—methanol)

IR (KBr): 1703, 1685, 1655 cm$^{-1}$

NMR (DMSO-d$_6$, δ): 2.0–2.2 (2H, m), 2.35–2.45 (2H, m), 2.85–3.0 (2H, m), 3.69 (2H, t, J=6.9 Hz), 4.2–4.3 (2H, m), 7.05–7.2 (1H, m), 7.23–7.4 (1H, m), 7.45–7.55 (1H, m), 7.82 (1H, s), 8.3–8.75 (4H, m), 9.33 (1H, s), 11.81 (1H, br s)

APCI-MS: 315 [M+H]$^+$

Anal. Calcd. for $C_{19}H_{19}ClN_4O_3 \cdot 0.5H_2O$: C 53.41, H 5.60, N 15.57 Found: C 53.44, H 5.33, N 15.47

(7) (2,3-Dihydro-9-hydroxy-1-benzoxepin-4-carbonyl)guanidine hydrochloride mp: 237–241° C. (dec.) (diisopropyl ether-methanol)

IR (Nujol): 3325, 1685, 1625, 1580 cm$^{-1}$

NMR (DMSO-d$_6$, δ): 2.85–2.95 (2H, m), 4.2–4.3 (2H, m), 6.85–7.1 (3H, m), 7.74 (1H, s), 8.3–8.75 (4H, m), 9.12(1H, s), 11.75 (1H, br s)

APCI-MS: 248 [M+H]$^+$

Anal Calcd. for $C_{12}H_{14}ClN_3O_3 \cdot 2.5H_2O$: C 43.84, H 5.83, N 12.78 Found: C 43.66, H 5.20, N 12.66

EXAMPLE 3

To a mixture of guanidine hydrochloride (0.25 g) and 28% sodium methoxide in methanol (0.49 ml) in N,N-dimethylformamide (1.5 ml) was added ethyl 9-carboxymethoxy-2,3-dihydro-1-benzoxepin-4-carboxylate (0.15 g) at room temperature. The mixture was stirred at room temperature for 24 hours. The mixture was poured into water, and the pH was adjusted to 6. The precipitates formed were collected by filtration, dissolved in aqueous sodium hydroxide solution and the pH of the solution was adjusted to 6 again. The precipitates were collected and washed with water, and suspended in methanol. The mixture was treated with methanesulfonic acid, and the solvent was evaporated in vacuo. The residue was recrystallized from a mixture of diisopropyl ether and methanol (1:1) to give (2,3-dihydro-9-methoxycarbonylmethoxy-1-benzoxepin-4-carbonyl)guanidine methanesulfonate (0.11 g).

mp: 185–187° C. (diisopropyl ether-methanol)

IR (KBr): 1734, 1697, 1637 cm$^{-1}$

NMR (DMSO-d$_6$, δ): 2.35 (3H, s), 2.85–3.0 (2H, m), 3.70 (3H, s), 4.2–4.35 (2H, m), 4.82(2H, s), 6.95–7.15 (3H, m), 7.37 (1H, s), 8.26 (4H, br s), 10.93 (1H, br s)

APCI-MS: 320 [M+H]$^+$

Anal Calcd. for $C_{16}H_{21}N_3O_8S \cdot 0.3H_2O$: C 45.67, H 5.17, N 9.99 Found: C 45.83, H 5.15, N 9.97

EXAMPLE 4

The following compounds were obtained according to a similar manner to that of Example 3.

(1) (9-Cyano-2,3-dihydro-1-benzoxepin-4-carbonyl)guanidine methanesulfonate mp: 242–244° C. (dec.) (diisopropyl ether-methanol)

IR (KBr): 2230, 1707 cm$^{-1}$

NMR (DMSO-d$_6$, δ): 2.36 (3H, s), 2.9–3.05 (2H, m), 4.4–4.55 (2H, m), 7.2–7.35 (1H, m), 7.41 (1H, s), 7.75–7.9 (2H, m), 8.29 (4H, br s), 11.02 (1H, br s)

APCI-MS: 257 [M+H]$^+$

Anal Calcd. for $C_{14}H_{16}N_4O_5 \cdot 0.4H_2O$: C 46.77, H 4.71, N 15.58 Found: C 46.30, H 4.67, N 15.97

(2) (2,3-Dihydro-9-hydroxymethyl-1-benzoxepin-4-carbonyl)guanidine methanesulfonate mp: 201–204° C. (dec.) (diisopropyl ether-methanol)

IR (KBr): 3330 (br), 1700 (br), 1633 cm$^{-1}$

NMR (DMSO-d$_6$, δ): 2.36 (3H, s), 2.85–3.0 (2H, m), 3.39 (1H, br s), 4.2–4.35 (2H, m), 4.54 (2H, br s), 7.05–7.2(1H, m), 7.35–7.55 (2H, m), 7.41 (1H, s), 8.29 (4H, br s), 10.94 (1H, br s)

APCI-MS: 262[M+H]$^+$

Anal Calcd. for $C_{14}H_{19}N_3O_6S \cdot 0.5H_2O$: C 45.90, H 5.50, N 11.47 Found: C 45.88, H 5.39, N 11.49

(3) (2,3-Dihydro-9-hydroxyiminomethyl-1-benzoxepin-4-carbonyl)guanidine methanesulfonate mp: 169–172° C. (dec.) (diisopropyl ether-methanol)

IR (KBr): 3350 (br), 1707, 1637, 1579 cm$^{-1}$

NMR (DMSO-d$_6$, δ): 2.37 (3H, s), 2.45–2.6 (2H, m), 4.25–4.45 (2H, m), 7.05–7.25 (1H, m), 7.40 (1H, s), 7.5–7.65 (1H, m), 7.65–7.8 (1H, m), 8.15–8.5 (5H, m), 10.97 (1H, br s), 11.37 (1H, br s)

APCI-MS: 275 [M+H]$^+$

Anal Calcd. for $C_{14}H_{18}N_4O_6S \cdot 0.5H_2O$: C 44.32, H 5.05, N 14.77 Found: C 44.01, H 4.84, N 15.07

(4) (9-Carboxy-2,3-dihydro-1-benzoxepin-4-carbonyl)guanidine methanesulfonate mp: 260–263° C. (dec.) (diisopropyl ether-methanol)

IR (KBr): 1730, 1690, 1635 cm$^{-1}$

NMR (DMSO-d$_6$, δ): 2.36 (3H, s), 2.9–3.0 (2H, m), 4.25–4.35 (2H, m), 7.1–7.25 (1H, m), 7.42 (1H, s), 7.55–7.7 (2H, m), 8.30 (4H, br s), 10.98 (1H, br s)

APCI-MS: 276 [M+H]$^+$

Anal Calcd. for $C_{14}H_{17}N_3O_7S \cdot 0.5H_2O$: C 44.21, H 4.77, N 11.05 Found: C 44.43, H 4.70, N 11.01

(5) (2,3-Dihydro-7-guanidinocarbonyl-1-benzoxepin-4-carbonyl)guanidine dihydrochloride mp: 311–313° C. (dec.) (diisopropyl ether-methanol)

IR (KBr): 3300, 1680 cm$^{-1}$

NMR (DMSO-d$_6$, δ): 2.85–3.05 (2H, m), 4.3–4.45 (2H, m), 7.19 (1H, d, J=8.6 Hz), 7.30 (1H, br s), 7.83 (1H, s), 8.18 (1H, dd, J=2.1, 8.6 Hz), 8.35 (1H, d, J=2.1 Hz), 8.35–8.8 (8H, m), 11.92 (2H, br s)

APCI-MS: 317 [M+H]$^+$

Anal Calcd. for $C_{14}H_{18}Cl_2N_6O_3 \cdot 1.5H_2O$: C 40.40, H 5.08, N 20.19 Found: C 40.49, H 4.95, N 20.01

(6) (2,3-Dihydro-9-methylthio-1-benzoxepin-4-carbonyl)guanidine hydrochloride mp: 220–221° C. (aqueous ethanol)

IR (Nujol): 3350, 3100, 1700, 1665, 1610, 1560 cm$^{-1}$

NMR (DMSO-d$_6$, δ): 2.39 (3H, s), 2.93 (2H, t, J=4.5 Hz), 4.30 (2H, t, J=4.5 Hz), 7.12 (1H, t, J=7.6 Hz), 7.22 (1H, dd, J=7.6 Hz), 7.37 (1H, d, J=7.6 Hz), 7.83 (1H, s), 8.44 (2H, br s), 8.68 (1H, br s), 11.87 (1H, s)

Anal Calcd. for $C_{13}H_{15}N_3O_2S \cdot HCl \cdot 0.15H_2O$: C 49.33, H 5.19, N 13.27 Found: C 49.28, H 5.08, N 13.10

EXAMPLE 5

A solution of (2,3-dihydro-9-methylthio-1-benzoxepin-4-carbonyl)guanidine hydrochloride (379 mg) in a mixture of chloroform and methanol (10:1, 50 ml) was cooled in an ice bath. To this solution was added 70% m-chloroperbenzoic acid (524 mg), and the mixture was stirred at 5–10° C. for 2 hours and at room temperature for 3.5 hours. The solvent was evaporated in vacuo and the residue was partitioned between aqueous potassium carbonate solution and ethyl acetate. The extract was washed successively with aqueous sodium thiosulfate solution and brine, dried over magnesium sulfate, and evaporated in vacuo to give pale yellow crystals, which were dissolved in a mixture of chloroform and methanol (10:1). The solution was cooled in an ice bath, and treated with 4N hydrogenechloride in 1,4-dioxane (1 ml). The solvent was evaporated in vacuo, and the residue was recrystallized from 95% ethanol to give (2,3-dihydro-9-methanesulfonyl-1-benzoxepin-4-carbonyl)guanidine hydrochloride (colorless crystals, 287 mg).

mp: 210–211° C.

IR (Nujol): 3330, 3160, 1680, 1560 cm$^{-1}$

NMR (DMSO-d$_6$, δ): 2.97–3.04 (2H, m), 3.32 (3H, s), 4.29–4.47 (2H, m), 7.34 (1H, t, J=7.7 Hz), 7.64–7.76 (1H, m), 7.84–7.93 (2H, m), 8.44 (2H, br s), 8.63 (2H, br s), 11.89 (1H, s)

Anal Calcd. for $C_{13}H_{15}N_3O_4S \cdot HCl \cdot 0.5H_2O$: C 44.00, H 4.82, N 11.84 Found: C 44.00, H 4.83, N 11.66

EXAMPLE 6

Under nitrogen atmosphere, 28% sodium methoxide in methanol (40.1 g) was added dropwise to a solution of guanidine hydrochloride (21.2 g) in N,N-dimethylformamide (50 ml) at 5° C. After the mixture was stirred at room temperature for 1 hour, a solution of ethyl 2,3-dihydro-9-methanesulfonyl-1-benzoxepin-4-carboxylate (13.1 g) in N,N-dimethylformamide (80 ml) was added dropwise to the mixture. The reaction mixture was stirred at room temperature for 16.5 hours, and poured into ice water (500 ml). The mixture was extracted with chloroform (200 ml×3), and the combined extracts were washed successively with water (200 ml×2) and brine. The solvent was removed under reduced pressure. The residue (9.50 g) was suspended in a mixture of chloroform and methanol (10:1) in an ice-bath, and methanesulfonic acid (3 ml) was added with stirring. The solvent was removed under reduced pressure to give 11.0 g of crude methanesulfonate, which was then recrystallized from aqueous ethanol (water:ethanol=1.4) to give (2,3-dihydro-9-methanesulfonyl-1-benzoxepin-4-carbonyl)guanidine methanesulfonate (colorless crystals, 6.07 g).

mp: 274–275° C.

IR (Nujol): 3380, 3290, 1685, 1635, 1585, 1560, 1300, 1155 $cm^{-1}$

NMR (DMSO-$d_6$, δ): 2.41 (3H, s), 3.02 (2H, t, J=4.6 Hz), 3.32 (3H, s), 4.46 (2H, t, J=4.6 Hz), 7.34 (1H, t, J=7.8 Hz), 7.48 (1H, s), 7.88 (2H, dd, J=1.6, 7.8 Hz), 8.36 (4H, br s), 11.08 (1H, s)

EXAMPLE 7

The following compounds were obtained according to a similar manner to that of Example 1.

(1) (2,3-Dihydro-9-ethoxycarbonylamino-1-benzoxepin-4-carbonyl)guanidine methanesulfonate mp: 199–201° C. (ethanol)

IR (Nujol): 3330, 1738, 1700, 1635 $cm^{-1}$

NMR (DMSO-$d_6$, δ): 1.24 (3H, t, J=7.1 Hz), 2.35 (3H, s), 2.85–3.0 (2H, m), 4.13 (2H, q, J=7.1 Hz), 4.05–4.15 (2H, m), 7.07 (1H, t, J=7.8 Hz), 7.20 (1H, d, J=7.8 Hz), 7.37 (1H, s), 7.78 (1H, d, J=7.8 Hz), 8.26 (4H, br s), 8.72(1H, s), 10.95 (1H, br s)

APCI-MS: 319 $[M+H]^+$ (2) (2,3-Dihydro-9-morphorinosulfonyl-1-benzoxepin-4-carbonyl)guanidine methanesulfonate mp: 150–151° C. (methanol-diisopropyl ether)

IR (Nujol): 3336, 1702, 1649 $cm^{-1}$

NMR (DMSO-$d_6$, δ): 2.38 (3H, s), 2.95–3.05 (2H, m), 3.10–3.20 (4H, m), 3.55–3.70 (4H, m), 4.30–4.50 (2H, m), 7.29 (1H, t, J=7.8 Hz), 7.45 (1H, s), 7.75–7.90 (2H, m), 8.20–8.50 (4H, br s), 11.05 (1H, s)

APCI-MS: 382$[M+H]^+$ (3) (9-Aminosulfonyl-2,3-dihydro-1-benzoxepin-4-carbonyl)guanidine methanesulfonate mp: 291–292° C. (isopropanol-water)

IR (Nujol): 3400, 3300, 3190, 1685, 1625, 1590, 1560 $cm^{-1}$

NMR (DMSO-$d_6$, δ): 2.40 (3H, s), 2.99 (2H, t, J=3.5 Hz), 4.42 (2H, t, J=3.5 Hz), 7.23(1H, t, J=7.7 Hz), 7.28 (2H, s), 7.46 (1H, s), 7.76 (1H, d, J=7.7 Hz), 7.79 (1H, dd, J=1.6, 7.7 Hz), 8.35 (4 H, br s), 11.04 (1H, s)

ESI-MS: 311$[M+H]^+$ (4) (2,3-Dihydro-9-trifluoromethyl-1-benzoxepin-4-carbonyl)guanidine methanesulfonate mp: 262–263° C. (methanol-diisopropyl ether)

IR (Nujol): 1693, 1633, 1591 $cm^{-1}$

NMR (DMSO-$d_6$, δ): 2.39 (3H, s), 2.90–3.05 (2H, m), 4.30–4.50 (2H, m), 7.29 (1H, t, J=7.7 Hz), 7.45 (1H, s), 7.71 (1H, d, J=7.7 Hz), 7.83 (1H, d, J=7.7 Hz), 8.15–8.55 (4 H, br s), 11.05 (1H, s)

APCI-MS: 300 $[M+H]^+$ (5) (2,3-Dihydro-9-methylaminosulfonyl-1-benzoxepin-4-carbonyl)guanidine methanesulfonate mp: 253–255° C. (methanol-diisopropyl ether)

IR (Nujol): 3284, 1709 $cm^{-1}$

NMR DMSO-$d_6$, δ): 2.39 (3H, s), 2.45 (3H, d, J=5.0 Hz), 2.90–3.05 (2H, m), 4.35–4.50 (2H, m), 7.20–7.40 (2H, m), 7.46 (1H, s), 7.80 (2H, d, J=7.8 Hz), 8.20–8.50 (4 H, br s)

APCI-MS: 325 $[M+H]^+$ (6) [2,3-Dihydro-9-[(dimethylsulfamoyl)amino]-1-benzoxepin-4-carbonyl]guanidine methanesulfonate mp: 231–233° C. (methanol-diisopropyl ether)

IR (Nujol): 3332, 3126, 1702$cm^{-1}$

NMR (DMSO-$d_6$, δ): 2.34 (3H, s), 2.68 (6 H, s), 2.90–3.05 (2H, m), 4.25–4.40 (2H, m), 7.07 (1H, t, J=7.8 Hz), 7.27 (1H, d, J=7.8 Hz), 7.36 (1H, s), 7.42 (1H, d, J=7.8 Hz), 8.10–8.40 (4 H, m), 9.16 (1H, s), 10.95 (1H, s)

APCI-MS: 355 $[M+H]^+$ (7) (2,3-Dihydro-9-sulfamoylamino-1-benzoxepin-4-carbonyl)guanidine methanesulfonate mp: 195–197° C. (methanol-diisopropyl ether)

IR (Nujol): 3327, 3211, 1709, 1649 $cm^{-1}$

NMR DMSO-$d_6$, δ): 2.36 (3H, s), 2.85–3.00 (2H, m), 4.20–4.40 (2H, m), 7.07 (1H, t, J=7.9 Hz), 7.13 (2H, br s), 7.20 (1H, d, J=7.9 Hz), 7.37 (1H, s), 7.46 (1H, d, J=7.9 Hz), 8.15–8.45 (4 H, br s), 8.41 (1H, s), 10.95 (1H, s)

APCI-MS: 326 $[M+H]^+$ (8) (2,3-Dihydro-9-carbamoyl-1-benzoxepin-4-carbonyl)-guanidine methanesulfonate mp: 255–257° C. (methanol-diisopropyl ether)

IR (Nujol): 3749, 3743, 1701, 1653 $cm^{-1}$

NMR (DMSO-$d_6$, δ): 2.38 (3H, s), 2.85–3.05 (2H, m), 4.30–4.50 (2H, m), 7.17 (1H, t, J=7.6 Hz), 7.44 (1H, s), 7.50–7.80 (4 H, m), 8.15–8.55 (4 H, br s), 10.98 (1H, s)

APCI-MS: 275 $[M+H]^+$

Preparation 39

The following compound was obtained according to a similar manner to that of Preparation 20.

Methyl 9-iodo-5-oxo-2,3,4,5-tetrahydro-1-benzoxepin-4-carboxylate mp: 100–101° C.

IR (Nujol): 1745, 1683, 1583$cm^{-1}$

NMR (DMSO-$d_6$, δ): 2.30–2.54 (2H, m), 3.65 (3H, s), 4.00–4.20 (2H, m), 4.41–4.54 (1H, m), 6.80 (1H, t, J=7.7 Hz), 7.64 (1H, dd, J=1.7 Hz, 7.7 Hz), 8.06 (1H, dd, J=1.7 Hz, 7.7 Hz)

Preparation 40

The following compound was obtained according to a similar manner to that of Preparation 22.

Methyl 5-hydroxy-9-iodo-2,3,4,5-tetrahydro-1-benzoxepin-4-carboxylate mp: 109–111° C.

IR (Nujol): 3315, 3129, 1707, 1689, 1652, 1631 $cm^{-1}$

NMR (DMSO-$d_6$, δ): 1.97–2.15 (1H, m), 2.22–2.40 (1H, m), 2.87–2.98 (1H, m), 3.59 (3H, s), 3.87–4.00 (1H, m), 4.10–4.24 (1H, m), 5.03–5.09 (1H, m), 5.60 (1H, d, J=4.8 Hz), 6.82 (1H, t, J=7.7 Hz), 7.33 (1H, dd, J=1.6 Hz, 7.7 Hz), 7.68 (1H, dd, J=1.6 Hz, 7.7 Hz)

Preparation 41

The following compound was obtained according to a similar manner to that of Preparation 24.

Methyl 2,3-dihydro-9-iodo-1-benzoxepin-4-carboxylate
mp: 63–64° C.
IR (Nujol): 1718, 1628 cm$^{-1}$
NMR (DMSO-d$_6$, δ): 2.91 (2H, t, J=4.7 Hz), 3.76 (3H, s), 4.29 (2H, t, J=4.7 Hz), 6.85 (1H, t, J=7.7 Hz), 7.49 (1H, s), 7.53(1H, dd, J=1.5 Hz, 7.7 Hz), 7.81 (1H, dd, J=1.5 Hz, 7.7 Hz)

Preparation 42

The following compound was obtained according to a similar manner to that of Preparation 12.

Methyl 2,3-dihydro-9-carboxy-1-benzoxepin-4-carboxylate
mp: 130–132° C.
IR (Nujol): 3477, 1701, 1684, 1651 cm$^{-1}$
NMR (DMSO-d$_6$, δ): 2.90 (2H, t, J=4.8 Hz), 3.76 (3H, s), 4.26 (2H, t, J=4.8 Hz), 7.11 (1H, t, J=7.6 Hz), 7.55 (1H, dd, J=1.6 Hz, 7.6 Hz), 7.56 (1H, s), 7.65 (1H, dd, J=1.6 Hz, 7.6 Hz)

Preparation 43

The following compounds were obtained according to a similar manner to that of Preparation 16.
(1) Methyl 2,3-dihydro-9-dimethylaminocarbonyl-1-benzoxepin-4-carboxylate
IR (Film): 1710, 1640 cm$^{-1}$
NMR (DMSO-d$_6$, δ): 2.77 (3H, s), 2.84–2.99 (2H, m), 2.98 (3H, s), 3.75 (3H, s), 4.21–4.29 (2H, m), 7.10 (1H, t, J=7.5 Hz), 7.20 (1H, dd, J=2.0 Hz, 7.5 Hz), 7.52–7.59 (2H, m)
(2) Methyl 2,3-dihydro-9-[2-tert-butoxycarbonylamino)-ethylaminocarbonyl]-1-benzoxepin-4-carboxylate
mp: 140–143° C.
IR (Nujol): 3371, 3334, 1714, 1682, 1635 cm$^{-1}$
NMR (DMSO-d$_6$, δ): 1.37 (9 H, s), 2.91 (2H, t, J=4.7 Hz), 3.06–3.16 (2H, m), 3.24–3.33 (2H, m), 3.76 (3H, s), 4.32 (2H, t, J=4.7 Hz), 6.88 (1H, t, J=5.0 Hz), 7.12 (1 H, t, J=7.6 Hz), 7.56–7.66 (3H, m), 8.27 (1H, t, J=5.5 Hz)

Preparation 44

To a mixture of methyl 2,3-dihydro-9-iodo-1-benzoxepin-4-carboxylate (15 g) and [1,1'-bis(diphenylphosphino)-ferrocene]dichloropalladium(II), complex with dichloromethane (1:1) (1.9 g) in N,N-dimethylformamide (225 ml) was introduced carbon monoxide for 15 minutes. To the mixture was added the triethylamine (15.8 ml) and triethylsilane (14.5 ml) and to the mixture was introduced carbon monoxide for 1hour. Additionally, the reaction mixture was stirred for 3 days at ambient temperature under carbon monoxide atmosphere. To the reaction mixture was added a mixture of ethyl acetate and water, and catalyst ws filtered off. The separated organic layer was washed with a water, dried over magnesium sulfate and evaporated in vacuo. The residue was triturated with a mixture of diisopropyl ether and hexane (1:1) to give methyl 2,3-dihydro-9-formyl-1-benzoxepin-4-carboxylate (7.7 g).
mp: 122–124° C.
IR (Nujol): 1710, 1670, 1630 cm$^{-1}$
NMR (DMSO-d$_6$, δ): 2.96 (2H, t, J=4.6 Hz), 3.77 (3H, s), 4.40 (2H, t, J=4.6 Hz), 7.20 (1H, t, J=7.6 Hz), 7.59 (1H, s), 7.70 (1H, dd, J=1.7 Hz, 7.6 Hz), 7.86 (1H, dd, J=1.7 Hz, 7.6 Hz)

Preparation 45

(Diethylamino)sulfur trifluoride (0.98 ml) was added to a solution of methyl 2,3-dihydro-9-formyl-1-benzoxepin-4-carboxylate (1.0 g) in dichloromethane (10 ml) under ice-cooling and the mixture was stirred at ambient temperature for 20 hours. To the reaction mixture was added a mixture of chloroform and water adjusted to pH 7 with 20% aqueous potassium carbonate. The separated organic layer was washed with water, dried over magnesium sulfate and evaporated in vacuo. The residue was purified by silica gel column chromatography using toluene to give a solid of methyl 2,3-dihydro-9-difluoromethyl-1-benzoxepin-4-carboxylate (0.77 g).
mp: 97–99° C.
IR (Nujol): 1711, 1633 cm$^{-1}$
NMR (DMSO-d$_6$, δ): 2.92 (2H, t, J=4.5 Hz), 3.76 (3H, s), 4.30 (2H, t, J=4.5 Hz), 7.16 (1H, t, J=55.2 Hz), 7.19 (1H, t, J=7.7 Hz), 7.54 (1H, d, J=7.7 Hz), 7.57 (1H, s), 7.70 (1H, d, J=7.7 Hz)

Preparation 46

Sodium borohydride (0.16 g) was added to a solution of methyl 2,3-dihydro-9-formyl-1-benzoxepin-4-carboxylate (1.6 g) in methanol (16 ml) and tetrahydrofuran (16 ml) under ice-cooling and the mixture was stirred at ambient temperature for 1hour. To the reaction mixture was added a mixture of ethyl acetate and water adjusted to pH 2with 1N hydrochloric acid. The separated organic layer was washed with water, dried over magnesium sulfate and evaporated in vacuo to give methyl 2,3-dihydro-9-hydroxymethyl-1-benzopexin-4-carboxylate (1.33g).
mp: 110–111° C.
IR (Nujol): 1711, 1637 cm$^{-1}$
NMR (DMSO-d$_6$, δ): 2.87 (2H, t, J=4.5 Hz), 3.74 (3H, s), 4.23 (2H, t, J=4.5 Hz), 4.54 (2H, d, J=5.6 Hz), 5.08 (1H, t, J=5.6 Hz), 7.05 (1H, t, J=7.8 Hz), 7.37 (1H, d, J=7.8 Hz), 7.42 (1H, d, J=7.8 Hz), 7.53 (1H, s)

Preparation 47

Under nitrogen atmosphere, phosphorus pentachloride (1.6 g) was added to a mixture of methyl 2,3-dihydro-9-hydroxymethyl-1-benzoxepin-4-carboxylate (1.2 g) and pyridine (0.62 ml) in dichloromethane (24 ml) under ice-cooling and the mixture was stirred at the same temperature for 2 hours. To the reaction mixture was added a mixture of ethyl acetate and water. The separated organic layer was washed with saturated aqueous sodium bicarbonate and water. The organic layer was dried over magnesium sulfate and evaporated in vacuo to give methyl 2,3-dihydro-9-chloromethyl-1-benzoxepin-4-carboxylate (1.19 g) as an oil.
IR (Nujol): 1710, 1633 cm$^{-1}$
NMR (DMSO-d$_6$, δ): 2.91 (2H, t, J=4.6 Hz), 3.76 (3H, s), 4.28 (2H, t, J=4.6 Hz), 4.75 (2H, s), 7.07 (1H, t, J=7.5 Hz), 7.46 (1H, d, J=7.5 Hz), 7.51 (1H, d, J=7.5 Hz), 7.54 (1H, s)

Preparation 48

28% Sodium methoxide in methanol (1.2ml) was added to a solution of methyl 2,3-dihydro-9-chloromethyl-1-benzoxepin-4-carboxylate (0.8 g) in methanol (8 ml) under ice-cooling and the mixture was stirred at the same temperature for 2 hours. The solvent was removed by concentration and to the residue was added a mixture of ethyl acetate and water. The separated organic layer was washed with water, dried over magnesium sulfate and evaporated in vacuo to give methyl 2,3-dihydro-9-methoxymethyl-1-benzoxepin-4-carboxylate (0.48 g).
mp: 76–78° C.
IR (Nujol): 1711, 1628 cm$^{-1}$
NMR (DMSO-d$_6$, δ): 2.88 (2H, t, J=4.5 Hz), 3.32 (3H, s), 3.75 (3H, s), 4.24 (2H, t, J=4.5 Hz), 4.44 (2H, s), 7.05 (1H, t, J=7.6 Hz), 7.35 (1H, d, J=7.6 Hz), 7.42 (1H, d, J=7.6 Hz), 7.53 (1H, s)

Preparation 49

The following compound was obtained according to a similar manner to that of Preparation 48.
Methyl 2,3-dihydro-9-methylthiomethyl-1-benzoxepin-4-carboxylate
IR (Nujol): 1710, 1633 cm$^{-1}$ NMR (DMSO-d$_6$, δ): 1.99 (3H, s), 2.88 (2H, t, J=4.4 Hz), 3.68 (2H, s), 3.75 (3H, s), 4.23 (2H, t, J=4.4 Hz), 7.02(1H, t, J=7.5 Hz), 7.28 (1H, dd, J=1.7 Hz, 7.5 Hz), 7.39 (1H, dd, J=1.7 Hz, 7.5 Hz), 7.53 (1H, s)

Preparation 50

The mixture of methyl 2,3-dihydro-9-formyl-1-benzoxepin-4-carboxylate (1.0 g), dimethylamine hydrochloride (0.7 g), triethylamine (1.2 ml) and 4 Å molecular sieves (1.0 g) in methanol (20 ml) and tetrahydrofuran (10 ml) was stirred at ambient temperature for 3 hours. To the mixture was added sodium borohydride (0.33 g) under ice-cooling and the mixture was stirred at ambient temperature for 20 hours. The solvent was removed by concentration. The residue was dissolved in a mixture of ethyl acetate and water and the mixture was adjusted to pH 1 with 6N hydrochloric acid. The separated aqueous layer was adjusted pH 10 with 20% aqueous potassium carbonate and extracted with a solution of ethyl acetate and tetrahydrofuran. The extract layer was washed with brine, dried over magnesium sulfate and evaporated to give methyl 2,3-dihydro-9-dimethylaminomethyl-1-benzoxepin-4-carboxylate (0.74 g).

IR (Film): 1705, 1633 cm$^{-1}$

NMR (DMSO-d$_6$, δ): 2.17 (6H, s), 2.87 (2H, t, J=4.8 Hz), 3.44 (2H, s), 3.75 (3H, s), 4.21 (2H, t, J=4.8 Hz), 7.03 (1H, t, J=7.5 Hz), 7.34 (1H, d, J=7.5 Hz), 7.38 (1H, d, J=7.5 Hz), 7.54 (1H, s)

Preparation 51

Methyl 2,3-dihydro-9-formyl-1-benzoxepin-4-carboxylate (0.5 g) was added to a mixture of O-methylhydroxylamine hydrochloride (0.25 g) and 28% sodium methoxide in methanol (0.5 ml) in methanol (5 ml) and the mixture was stirred at ambient temperature for 4 hours. The reaction mixture was partitioned between ethyl acetate and water. The organic layer was washed with brine, dried over magnesium sulfate, and evaporated in vacuo to give methyl 2,3-dihydro-9-methoxyiminomethyl-1-benzoxepin-4-carboxylate (0.55 g).

mp: 70–74° C.

IR (Nujol): 1701, 1630 cm$^{-1}$

NMR (DMSO-d$_6$, δ): 2.90 (2H, t, J=4.3 Hz), 3.76 (3H, s), 3.90 (3H, s), 4.28 (2H, t, J=4.3 Hz), 7.09 (1H, t, J=7.7 Hz), 7.53 (1H, s), 7.57 (1H, dd, J=1.6 Hz, 7.7 Hz), 7.68 (1H, dd, J=1.6 Hz, 7.7 Hz), 8.42 (1H, s)

Preparation 52

A solution of potassium peroxymonosulfate (6.7 g) in water (33 ml) was added dropwise to a mixture of ethyl 2,3-dihydro-9-methylthio-1-benzoxepin-4-carboxylate (2.6 g) and tetrabutylammonium hydrogen sulfate (0.7 g) in ethyl acetate (26 ml) and water (13 ml) and the mixture was stirred at ambient temperature for 2.5 hours. The separated organic layer was washed with 10% aqueous sodium thiosulfate. The organic layer was washed with water, dried over magnesium sulfate and evaporated in vacuo. The residue was purified by column chromatography on silica gel using a mixture of ethyl acetate and toluene (1:1) as an eluent. The eluted fractions containing the desired product were collected and evaporated in vacuo to give ethyl 2,3-dihydro-9-methanesulfinyl-1-benzoxepin-4-carboxylate (0.65 g).

mp: 75–77° C.

IR (Nujol): 1705, 1633, 1045 cm$^{-1}$

NMR (DMSO-d$_6$, δ): 1.28 (3H, t, J=7.0 Hz), 2.74 (3H, s), 2.93 (2H, t, J=4.6 Hz), 4.20 (2H, q, J=7.0 Hz), 4.35 (2H, t, J=4.6 Hz), 7.33 (1H, t, J=7.6 Hz), 7.58 (1H, s), 7.67 (1H, dd, J=1.6 Hz, 7.6 Hz), 7.70 (1H, dd, J=1.6 Hz, 7.6 Hz)

(+) APCI-MS: 281 (M$^+$+H)$^+$

Preparation 53

The mixture of ethyl 2,3-dihydro-7-amino-1-benzoxepin-4-carboxylate (2.0 g), dimethyl disulfide (2.3 ml) and t-butylnitrile (1.2 ml) in acetonitrile (4 ml) was stirred at 50° C. for 2.5 hours. The mixture was poured into a mixture of ethyl acetate and water. The separated organic layer was washed with water, dried over magnesium sulfate and evaporated in vacuo. The residue was purified by column chromatography on silica gel using a mixture of hexane and toluene (1:1) as an eluent. The eluted fractions containing the desired product were collected and evaporated in vacuo to give ethyl 2,3-dihydro-7-methylthio-1-benzoxepin-4-carboxylate (1.24 g).

mp: 46–48° C.

IR (Nujol): 1695 cm$^{-1}$

NMR (DMSO-d$_6$, δ): 1.28 (3H, t, J=7.1 Hz), 2.47 (3H, s), 2.87 (2H, t, J=4.3 Hz), 4.13–4.27 (4H, m), 6.93 (1H, d, J=8.5 Hz), 7.21 (1H, dd, J=2.4 Hz, 8.5 Hz), 7.42 (1H, d, J=2.4 Hz), 7.53 (1H, s)

(+) APCI-MS: 265 (M$^+$+H)$^+$

Preparation 54

The following compounds were obtained according to a similar manner to that of Preparation 53.

(1) Ethyl 2,3-dihydro-9-ethylthio-1-benzoxepin-4-carboxylate mp: 53–56° C.

IR (Nujol): 1697, 1630 cm$^{-1}$

NMR (DMSO-d$_6$, δ): 1.20–1.33 (6H, m), 2.83–2.95 (4H, m), 4.14–4.29 (4H, m), 7.05 (1H, t, J=7.6 Hz), 7.24 (1H, d, J=7.6 Hz), 7.28 (1H, d, J=7.6 Hz), 7.49 (1H, s)

(+) APCI-MS: 279 (M$^+$+H)$^+$ (2) Methyl 2,3-dihydro-7-chloro-9-methylthio-1-benzoxepin-4-carboxylate mp: 140–142° C.

IR (Nujol): 1699, 1630 cm$^{-1}$

NMR (DMSO-d$_6$, δ): 2.41 (3H, s), 290 (2H, t, J=4.5 Hz), 3.75 (3H, s), 4.27 (2H, t, J=4.5 Hz), 7.12 (1H, d, J=2.4 Hz), 7.41 (1H, d, J=2.4 Hz), 7.47 (1H, s)

Preparation 55

A solution of potassium peroxymonosulfate (4.1 g) in water (21 ml) was added dropwise to a mixture of ethyl 2,3-dihydro-7-methylthio-1-benzoxepin-4-carboxylate (0.8 g) and tetrabutylammonium hydrogen sulfate (0.2 g) in ethyl acetate (8 ml) and water (4 ml) at ambient temperature and the mixture was stirred at the same temperature for 3 hours. The separated organic layer was washed with 10% aqueous sodium thiosulfate. The organic layer was washed with water, dried over magnesium sulfate and evaporated in vacuo to give ethyl 2,3-dihydro-7-methanesulfonyl-1-benzoxepin-4-carboxylate (0.77 g).

mp: 174–176° C.

IR (Nujol): 1701, 1302, 1146 cm$^{-1}$

NMR (DMSO-d$_6$, δ): 1.29 (3H, t, J=7.1 Hz), 2.93 (2H, t, J=4.5 Hz), 3.22 (3H, s), 4.22 (2H, q, J=7.1 Hz), 4.33 (2H, t, J=4.5 Hz), 7.19 (1H, d, J=8.6 Hz), 7.62 (1H, s), 7.79 (1H, dd, J=2.3 Hz, 8.6 Hz), 8.12 (1H, d, J=2.3 Hz)

(+) APCI-MS: 297 (M$^+$+H)$^+$

Preparation 56

The following compounds were obtained according to a similar manner to that of Preparation 55.

(1) Ethyl 2,3-dihydro-9-ethanesulfonyl-1-benzoxepin-4-carboxylate mp: 81–83° C.

IR (Nujol): 1705, 1631, 1308, 1128 cm$^{-1}$

NMR (DMSO-d$_6$, δ): 1.12 (3H, t, J=7.4 Hz), 1.29 (3H, t, J=7.1 Hz), 2.96 (2H, t, J=4.4 Hz), 3.43 (2H, q, J=7.4 Hz), 4.23 (2H, q, J=7.1 Hz), 4.39 (2H, t, J=4.4 Hz), 7.30 (1H, t, J=7.7 Hz), 7.60 (1H, s), 7.81 (1H, dd, J=1.6 Hz, 7.7 Hz), 7.91 (1H, dd, J=1.6 Hz, 7.7 Hz)

(+) APCI-MS: 311 (M$^+$+H)$^+$ (2) Ethyl 2,3-dihydro-7-chloro-9-methanesulfonyl-1-benzoxepin-4-carboxylate mp: 160–162° C.

IR (Nujol): 1703, 1630, 1140 cm$^{-1}$

NMR (DMSO-d$_6$, δ): 2.98 (2H, t, J=4.5 Hz), 3.34 (3H, s), 3.77 (3H, s), 4.22 (2H, t, J=4.5 Hz), 7.61 (1H, s), 7.73 (1H, d, J=2.7 Hz), 8.12 (1H, d, J=2.7 Hz)

(+) APCI-MS: 317 (M$^+$+H)$^+$

Preparation 57

Methyl 2,3-dihydro-7-chloro-1-benzoxepin-4-carboxylate (1.0 g) was added to nitric acid (4.5 ml, d=1.42) under ice-cooling and the mixture was stirred at ambient temperature for 2 hours. The mixture was poured into water and the isolated precipitate was collected by filtration to give methyl 2,3-dihydro-7-chloro-9-nitro-1-benzoxepin-4-carboxylate (1.04 g).

mp: 134–137° C.

IR (Nujol): 1710, 1637, 1527 cm$^{-1}$

NMR (DMSO-d$_6$, δ): 2.96 (2H, t, J=4.5 Hz), 3.77 (3H, s), 4.36 (2H, t, J=4.5 Hz), 7.60 (1H, s), 7.99–8.07 (2H, m)

Preparation 58

To a suspension of iron (reduced, 13.6 g) and ammonium chloride (1.6 g) in a mixture of methanol (140 ml) and water (50 ml) was added methyl 2,3-dihydro-7-chloro-9-nitro-1-benzoxepin-4-carboxylate (13.8 g) in portions under reflux. The reaction mixture was stirred for 6 hours under reflux. The iron powder was filtered off and the solvent was removed by concentration. The residue was diluted with ethyl acetate. The organic solvent was washed successively with saturated aqueous sodium bicarbonate and water, dried over magnesium sulfate, and evaporated in vacuo. The residue was purified by column chromatography on silica gel using chloroform as an eluent. The eluted fractions containing the desired product were collected and evaporated in vacuo to give methyl 2,3-dihydro-7-chloro-9-amino-1-benzoxepin-4-carboxylate (6.8 g).

mp: 115–118° C.

IR (Nujol): 3481, 3379, 1693, 1616 cm$^{-1}$

NMR (DMSO-d$_6$, δ): 2.87 (2H, t, J=4.5 Hz), 3.74 (3H, s), 4.21 (2H, t, J=4.5 Hz), 5.25 (2H, s), 6.65–6.72 (2H, m), 7.37 (1H, s)

EXAMPLE 8

Under nitrogen atmosphere, 28% sodium methoxide in methanol (5.5 ml) was added to a solution of methyl 2,3-dihydro-9-carboxy-1-benzoxepin-4-carboxylate (1.5 g) and guanidine hydrochloride (2.9 g) in N,N-dimethylformamide (15 ml) at ambient temperature. The mixture was stirred at the same temperature for 18 hours. The reaction mixture was poured into water and the mixture was adjusted to pH 6.5 with 6N hydrochloric acid. The isolated precipitate was collected by filtration to give (2,3-dihydro-9-carboxy-1-benzoxepin-4-carbonyl)guanidine (1.11 g).

NMR (DMSO-d$_6$, δ): 2.95 (2H, t, J=4.5 Hz), 4.21 (2H, t, J=4.5 Hz), 7.03 (1H, t, J=7.6 Hz), 7.35–7.47 (2H, m), 7.58 (1H, s)

EXAMPLE 9

2M (Trimethylsilyl)diazomethane in hexane (1.8 ml) was added to a solution of (2,3-dihydro-9-carboxy-1-benzoxepin-4-carbonyl)guanidine (0.5 g) in N,N-dimethylformamide (10 ml) and methanol (5 ml) and the mixture was stirred at ambient temperature for 1 hour. To the reaction mixture was added acetic acid (1 ml) and stirred for 15 minutes. The mixture was poured into a mixture of ethyl acetate and water, and the mixture was adjusted to pH 9 with 20% aqueous potassium carbonate. The separated organic layer was washed with water, dried over magnesium sulfate and evaporated in vacuo. The residue was purified by column chromatography on silica gel using a mixture of chloroform and methanol (9:1) as an eluent. The eluted fractions containing the desired product were collected and evaporated in vacuo. The residue (0.16 g) was dissolved in methanol (5 ml), and methanesulfonic acid (0.1 ml) was added with stirring. The crystalline was collected by filtration and recrystallized from a mixture of methanol and diisopropyl ether to give (2,3-dihydro-9-methoxycarbonyl-1-benzoxepin-4-carbonyl)guanidine methanesulfonate (0.14 g).

mp: 195–197° C.

IR (Nujol): 3352, 3132, 1726, 1699, 1178, 1078 cm$^{-1}$

NMR (DMSO-d$_6$, δ): 2.38 (3H, s), 2.94 (2H, t, J=4.7 Hz), 3.82 (3H, s), 4.31 (2H, t, J=4.7 Hz), 7.19 (1H, t, J=7.6 Hz), 7.43 (1H, s), 7.61 (1H, dd, J=1.7 Hz, 7.6 Hz), 7.70 (1H, dd, J=1.7 Hz, 7.6 Hz), 8.31 (4H, s), 11.01 (1H, s)

(+) APCI-MS: 290 (M$^+$+H)$^+$

EXAMPLE 10

The following compounds were obtained according to a similar manner to that of Example 6.

(1) (2,3-Dihydro-9-dimethylaminocarbonyl-1-benzoxepin-4-carbonyl)guanidine methanesulfonate mp: 116–118° C.

IR (Nujol): 3323, 1699, 1682, 1639, 1246 cm$^{-1}$

NMR (DMSO-d$_6$, δ): 2.44 (3H, s), 2.78 (3H, s), 2.90–2.96 (2H, m), 2.99 (3H, s), 4.20–4.40 (2H, m), 7.16 (1H, t, J=7.4 Hz), 7.24 (1H, dd, J=2.0 Hz, 7.4 Hz), 7.46 (1H, s), 7.58 (1H, dd, J=2.0 Hz, 7.4 Hz), 8.39 (4H, s), 11.05 (1H, s)

(+) APCI-MS: 303 (M$^+$+H)$^+$ (2) (2,3-Dihydro-9-methoxyiminomethyl-1-benzoxepin-4-carbonyl)guanidine methanesulfonate mp: 212–213° C.

IR (Nujol): 3359, 3323, 3132, 1701, 1691, 1602, 1192 cm$^{-1}$

NMR (DMSO-d$_6$, δ): 2.42 (3H, s), 2.94 (2H, t, J=4.6 Hz), 3.90 (3H, s), 4.33 (2H, t, J=4.6 Hz), 7.15 (1H, t, J=7.7 Hz), 7.42 (1H, s), 7.60 (1H, dd, J=1.6 Hz, 7.7 Hz), 7.72 (1H, dd, J=1.6 Hz, 7.7 Hz), 8.36 (4H, s), 8.43 (1H, s), 11.04 (1H, s)

(+) APCI-MS: 289 (M$^+$+H)$^+$ (3) (2,3-Dihydro-9-methanesulfinyl-1-benzoxepin-4-carbonyl)guanidine methanesulfonate mp: 224–225° C.

IR (Nujol): 3394, 3325, 3130, 1709, 1684, 1651, 1637, 1595, 1171, 1043 cm$^{-1}$ NMR (DMSO-d$_6$, δ): 2.41 (3H, s), 2.76 (3H, s), 2.97 (2H, t, J=4.6 Hz), 4.37 (2H, t, J=4.6 Hz), 7.38 (1H, t, J=7.6 Hz), 7.46 (1H, s), 7.70 (2H, d, J=7.6 Hz), 8.35 (4H, s), 11.06 (1H, s)

(+) APCI-MS: 294 (M$^+$+H)$^+$ (4) (2,3-Dihydro-7-methylthio-1-benzoxepin-4-carbonyl)guanidine methanesulfonate mp: 219–221° C.

IR (Nujol): 3369, 3321, 3145, 1695, 1689, 1639, 1190, 1047 cm$^{-1}$

NMR (DMSO-d$_6$, δ): 2.43 (3H, s), 2.48 (3H, s), 2.90 (2H, t, J=4.5 Hz), 4.24 (2H, t, J=4.5 Hz), 6.98 (1H, d, J=8.5 Hz), 7.27 (1H, dd, J=2.4 Hz, 8.5 Hz), 7.43 (1H, s), 7.44 (1H, d, J=2.4 Hz), 8.37 (4H, s), 11.02 (1H, s)

(+) APCI-MS: 278 (M$^+$+H)$^+$ (5) (2,3-Dihydro-9-ethylthio-1-benzoxepin-4-carbonyl)guanidine methanesulfonate mp: 222–224° C.

IR (Nujol): 3356, 3130, 1701, 1659, 1635, 1606, 1176, 1051 cm$^{-1}$

NMR (DMSO-d$_6$, δ): 1.26 (3H, t, J=7.3 Hz), 2.43 (3H, s), 2.85–2.98 (4H, m), 4.30 (2H, t, J=4.6 Hz), 7.10 (1H, t, J=7.4 Hz), 7.28 (1H, d, J=7.4 Hz), 7.31 (1H, d, J=7.4 Hz), 7.39 (1H, s), 8.37 (4H, s), 11.02 (1H, s)

(+) APCI-MS: 292 (M$^+$+H)$^+$ (6) (2,3-Dihydro-9-ethanesulfonyl-1-benzoxepin-4-carbonyl)guanidine methanesulfonate mp: 234–235° C.

IR (Nujol): 3384, 3319, 3159, 1707, 1687, 1639, 1313, 1161, 1043 cm$^{-1}$

NMR (DMSO-d$_6$, δ): 1.12 (3H, t, J=7.4 Hz), 2.41 (3H, s), 3.01 (2H, t, J=4.5 Hz), 3.44 (2H, q, J=7.4 Hz), 4.43 (2H, t, J=4.5 Hz), 7.35 (1H, t, J=7.7 Hz), 7.48 (1H, s), 7.86 (1H, d, J=7.7 Hz), 7.90 (1H, d, J=7.7 Hz), 8.36 (4H, s), 11.08 (1H, s)

(+) APCI-MS: 324 (M$^+$+H)$^+$ (7) (2,3-Dihydro-7-chloro-9-methylthio-1-benzoxepin-4-carbonyl)guanidine methanesulfonate mp: 283–285° C.

IR (Nujol): 3350, 1699, 1657, 1639, 1610, 1173, 1051 cm$^{-1}$

NMR (DMSO-d$_6$, δ): 2.37 (3H, s), 2.43 (3H, s), 2.94 (2H, t, J=4.5 Hz), 4.32 (2H, t, J=4.5 Hz), 7.17 (1H, d, J=2.4 Hz), 7.33 (1H, s), 7.36 (1H, d, J=2.4 Hz), 8.29 (4H, s), 10.97 (1H, s)

(+) APCI-MS: 312 (M$^+$+H)$^+$ (8) (2,3-Dihydro-7-chloro-9-methanesulfonyl-1-benzoxepin-4-carbonyl)guanidine methanesulfonate mp: 288–289° C.

IR (Nujol): 3302, 1705, 1687, 1639, 1308, 1169, 1039 cm$^{-1}$

NMR (DMSO-d$_6$, δ): 2.38 (3H, s), 3.03 (2H, t, J=4.7 Hz), 3.36 (3H, s), 4.47 (2H, t, J=4.7 Hz), 7.45 (1H, s), 7.78 (1H, d, J=2.6 Hz), 8.03 (1H, d, J=2.6 Hz), 8.34 (4H, s), 11.04 (1H, s)

(+) APCI-MS: 344 (M$^+$+H)$^+$ (9) (2,3-Dihydro-7-methanesulfonyl-1-benzoxepin-4-carbonyl)guanidine methanesulfonate mp: 231–232° C.

IR (Nujol): 3315, 3130, 1707, 1689, 1595, 1306, 1180, 1043 cm$^{-1}$

NMR (DMSO-d$_6$, δ): 2.46 (3H, s), 2.96 (2H, t, J=4.3 Hz), 3.23 (3H, s), 4.37 (2H, t, J=4.3 Hz), 7.24 (1H, d, J=8.6 Hz), 7.54 (1H, s), 7.85 (1H, dd, J=2.2 Hz, 8.6 Hz), 8.11 (1H, d, J=2.2 Hz), 8.39 (4H, s), 11.12 (1H, s)

(+) APCI-MS: 310 (M$^+$+H)$^+$

(10) (2,3-Dihydro-9-difluoromethyl-1-benzoxepin-4-carbonyl)guanidine methanesulfonate mp: 249–251° C.

IR (Nujol): 3323, 3140, 1703, 1660, 1641, 1203, 1028 cm$^{-1}$

NMR (DMSO-d$_6$, δ): 2.42 (3H, s), 2.96 (2H, t, J=4.5 Hz), 4.34 (2H, t, J=4.5 Hz), 7.17 (1H, t, J=55.1 Hz), 7.24 (1H, t, J=7.7 Hz), 7.45 (1H, s), 7.59 (1H, d, J=7.7 Hz), 7.71 (1H, d, J=7.7 Hz), 8.38 (4H, s), 11.07 (1H, s)

(+) APCI-MS: 282 (M$^+$+H)$^+$

(11) (2,3-Dihydro-9-methoxymethyl-1-benzoxepin-4-carbonyl)guanidine methanesulfonate mp: 180–182° C.

IR (Nujol): 3357, 3143, 1703, 1691, 1658, 1637, 1194 cm$^{-1}$

NMR (DMSO-d$_6$, δ): 2.42 (3H, s), 2.92 (2H, t, J=4.6 Hz), 3.34 (3H, s), 4.29 (2H, t, J=4.6 Hz), 4.46 (2H, s), 7.11 (1H, t, J=7.5 Hz), 7.35–7.49 (3H, m), 8.34 (4H, s), 10.99 (1H, s)

(+) APCI-MS: 276 (M$^+$+H)$^+$

(12) (2,3-Dihydro-9-dimethylaminomethyl-1-benzoxepin-4-carbonyl)guanidine dihydrochloride mp: 279–280° C.

IR (Nujol): 1689, 1630 cm$^{-1}$

NMR (DMSO-d$_6$, δ): 2.72 (6H, s), 2.97 (2H, t, J=4.5 Hz), 4.31 (2H, s), 4.37 (2H, t, J=4.5 Hz), 7.19 (1H, t, J=7.6 Hz), 7.64 (1H, d, J=7.6 Hz), 7.72 (1H, d, J=7.6 Hz), 8.00 (1H, s), 8.64 (2H, s), 8.84 (2H, s), 10.48 (1H, s), 12.17 (1H, s)

EXAMPLE 11

To a mixture of methyl 2,3-dihydro-9-[2-(tert-butoxycarbonylamino)ethylaminocarbonyl]-1-benzoxepin-4-carboxylate (1.1 g) and guanidine hydrochloride (1.3 g) in N,N-dimethylformamide (11 ml) was added 28% sodium methoxide in methanol (2.6 ml). The reaction mixture was stirred for 8 hours at ambient temperature, and the mixture was poured into a mixture of ethyl acetate and water. The separated organic layer was washed with water, dried over magnesium sulfate and evaporated in vacuo to give {2,3-dihydro-9-[2-(tert-butoxycarbonylamino)ethylaminocarbonyl]-1-benzoxepin-4-carbonyl}guanidine (0.9 g) as an oil.

IR (Film): 3340, 1714, 1699, 1684, 1670, 1649 cm$^{-1}$

NMR (DMSO-d$_6$, δ): 1.38 (9H, s), 2.93–2.99 (2H, m), 3.08–3.15 (2H, m), 3.25–3.36 (2H, m), 4.29 (2H, t, J=4.7 Hz), 6.85–6.90 (1H, m), 7.08 (1H, t, J=7.6 Hz), 7.43 (1H, d, J=7.6 Hz), 7.56 (1H, d, J=7.6 Hz), 7.62 (1H, s), 8.28 (1H, t, J=5.6 Hz)

EXAMPLE 12

The following compound was obtained according to a similar manner to that of Example 11.

(2,3-Dihydro-9-methylthiomethyl-1-benzoxepin-4-carbonyl)guanidine mp: 140–143° C.

IR (Nujol): 3354, 1633 cm$^{-1}$

NMR (DMSO-d$_6$, δ): 1.99 (3H, s), 2.93 (2H, t, J=4.5 Hz), 3.67 (2H, s), 4.19 (2H, t, J=4.5 Hz), 6.20–8.40 (4H, br s), 6.97 (1H, t, J=7.5 Hz), 7.18 (1H, d, J=7.5 Hz), 7.22 (1H, d, J=7.5 Hz), 7.59 (1H, s)

EXAMPLE 13

Methanesulfonic acid (0.04 ml) was added to the mixture of (2,3-dihydro-9-methylthiomethyl-1-benzoxepin-4-carbonyl)guanidine (0.15 g) in methanol (1.5 ml) and the mixture was stirred at ambient temperature for 30 minutes. To the mixture was added diisopropyl ether (3 ml). The isolated crystalline was collected by filtration and recrystallized from a mixture of methanol and diisopropyl ether to give (2,3-dihydro-9-methylthiocarbonyl-1-benzoxepin-4-carbonyl)guanidine methanesulfonate (0.12 g).

mp: 160–162° C.

IR (Nujol): 3342, 3126, 1703, 1691, 1658, 1608, 1173, 1047 cm$^{-1}$

NMR (DMSO-d$_6$, δ): 1.99 (3H, s), 2.41 (3H, s), 2.93 (2H, t, J=4.6 Hz), 3.67 (2H, s), 4.28 (2H, t, J=4.6 Hz), 7.07 (1H, t, J=7.6 Hz), 7.33 (1H, d, J=7.6 Hz), 7.42 (1H, s), 7.43 (1H, d, J=7.6 Hz), 8.35 (4H, s), 10.99 (1H, s)

(+) APCI-MS: 292 (M$^+$+H)$^+$

EXAMPLE 14

The mixture of (2,3-dihydro-9-methylthiomethyl-1-benzoxepin-4-carbonyl)guanidine (0.4 g) and m-chloroperbenzoic acid (0.52 g) in chloroform (20 ml) and methanol (4 ml) was stirred at ambient temperature for 2 hours. The reaction mixture was added to 10% aqueous sodium thiosulfate, adjusted to pH 9 with 20% aqueous potassium carbonate and extracted with a mixture of ethyl acetate and tetrahydrofuran. The extract layer was washed with water, dried over magnesium sulfate and evaporated in vacuo. The residue was dissolved in methanol (5 ml), and methanesulfonic acid (0.11 ml) was added with stirring. To the mixture was added diisopropyl ether (5 ml) and isolated crystalline was collected by filtration. The crystalline was recrystallized from a mixture of methanol and diisopropyl ether to give (2,3-dihydro-9-methanesulfonylmethyl-1-benzoxepin-4-carbonyl)guanidine methanesulfonate (0.16 g).

mp: 138–141° C.

IR (Nujol): 3332, 3132, 1703, 1687, 1637, 1169, 1047 cm$^{-1}$

NMR (DMSO-d$_6$, δ): 2.42 (3H, s), 2.90–3.04 (5H, m), 4.29 (2H, t, J=4.6 Hz), 4.53 (2H, s), 7.16 (1H, t, J=7.6 Hz), 7.41–7.50 (2H, m), 7.56 (1H, dd, J=1.4 Hz, 7.6 Hz), 8.37 (4H, s), 11.02 (1H, s)

(+) APCI-MS: 324 (M$^+$+H)$^+$

EXAMPLE 15

To a solution of {2,3-dihydro-9-[2-(tert-butoxycarbonylamino)ethylaminocarbonyl]-1-benzoxepin-4-carbonyl}guanidine (0.8 g) in 1,4-dioxane (8 ml) was added 4N hydrogen chloride in 1,4-dioxane (8 ml) at ambient temperature and the mixture was stirred at the same temperature for 18 hours. Diisopropyl ether (10 ml) was added to the mixture and the precipitate was collected by filtration. The precipitate was recrystallized from a mixture of methanol and diisopropyl ether to give [2,3-dihydro-9-(2-aminoethylaminocarbonyl)-1-benzoxepin-4-carbonyl]guanidine dihydrochloride (0.57 g).

mp: 158–160° C.

IR (Nujol): 3398, 1701, 1630, 1618 cm$^{-1}$

NMR (DMSO-d$_6$, δ): 2.86–3.10 (4H, m), 3.48–3.64 (2H, m), 4.39 (2H, t, J=4.6 Hz), 7.19 (1H, t, J=7.6 Hz), 7.74 (2H, d, J=7.6 Hz), 7.97 (1H, s), 8.13 (3H, s), 8.53 (1H, t, J=5.8 Hz), 8.59 (2H, s), 8.81 (2H, s), 12.11 (1H, s)

(+) APCI-MS: 318 (M$^+$+H)$^+$

What is claimed is:

1. A compound of the formula:

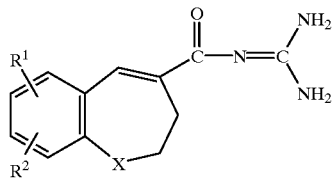

wherein R$^1$ is hydrogen or halogen,

R$^2$ is hydroxy, acyl(lower)alkoxy, hydroxy(lower)alkyl, lower alkoxy(lower)alkyl, lower alkylthio(lower)alkyl, mono(or di or tri)halo(lower)alkyl, (ethoxycarbonyl) amino, sulfamoylamino, (dimethylsulfamoyl)amino, N,N-di(lower)alkylamino(lower)alkyl, hydroxyimino (lower)alkyl, lower alkoxyimino(lower)alkyl, acyl, lower alkoxycarbonyl, carbamoyl, di(lower)alkylcarbamoyl, (amino(lower)alkyl)carbamoyl, N,N-di(lower)alkylamino(lower)alkylcarbamoyl, guanidinocarbonyl, morpholinylsulfonyl, sulfamoyl, lower alkylsulfamoyl, (lower alkylsulfonyl) (lower) alkyl, guanidinocarbonyl(lower)alkenyl, lower alkylthio, cyano, acyl(lower)alkyl, acyl(lower)alkenyl, aryl which has one or more substituent(s) or a heterocyclic group which has one or more substituent(s), and X is —O—, or a salt thereof.

2. A compound of claim 1,

R$^1$ is hydrogen or halogen,

R$^2$ is hydroxy, lower alkoxycarbonyl(lower)alkoxy, hydroxy(lower)alkyl, lower alkoxy(lower)alkyl, lower alkylthio(lower)alkyl, dihalo(lower)alkyl, trihalo(lower)alkyl, (ethoxycarbonyl)amino, sulfamoylamino, (dimethylsulfamoyl)amino, N,N-di(lower)alkylamino (lower)alkyl, hydroxyimino(lower)alkyl, lower alkoxyimino(lower)alkyl, carboxy, lower alkoxycarbonyl, carbamoyl, di(lower)alkylcarbamoyl, (amino(lower)alkyl)carbamoyl, N,N-di(lower) alkylamino(lower)alkylcarbamoyl, guanidinocarbonyl, lower alkylsulfonyl, lower alkylsulfinyl, morpholinylsulfonyl, sulfamoyl, lower alkylsulfamoyl, lower alkylthio, cyano, (lower alkylsulfonyl) (lower) alkyl, carboxy(lower)alkenyl, guanidinocarbonyl (lower)alkenyl, phenyl, which has one to four hydroxy (lower)alkyl substituents, thienyl which has one to three halogen substituents, or pyrrolidinyl which has one to four oxo substituents, and X is —O—.

3. A compound of claim 2, wherein

R$^1$ is hydrogen or halogen, and

R$^2$ is guanidinocarbonyl or lower alkylsulfonyl.

4. A compound of claim 3, which is selected from the group consisting of:

(1) (2,3-Dihydro-9-methanesulfonyl-1-benzoxepin-4-carbonyl)guanidine or its hydrochloride or methanesulfonate, (2) (2,3-Dihydro-7-chloro-9-methanesulfonyl-1-benzoxepin-4-carbonyl)guanidine, and (3) (2,3-Dihydro-9-guanidinocarbonyl-1-benzoxepin-4-carbonyl)guanidine or its dihydrochloride.

5. A pharmaceutical composition which comprises, as an active ingredient, a compound of claim 1 or a pharmaceutically acceptable salt thereof in admixture with pharmaceutically acceptable carriers.

6. A method for inhibiting Na$^+$/H$^+$ exchange in cells comprising:

administering to a patient in need thereof an amount of a compound of claim 1 effective to inhibit Na$^+$/H$^+$ exchange.

7. A method for treatment of cardiovascular diseases, cerebrovascular diseases, renal diseases, arteriosclerosis or shock which comprises administering a compound of claim 1 or a pharmaceutically acceptable salt thereof to a human being or animal.

* * * * *